(12) United States Patent
Shipp et al.

(10) Patent No.: US 9,939,428 B2
(45) Date of Patent: Apr. 10, 2018

(54) COMPOSITIONS, KITS, AND METHODS FOR THE DIAGNOSIS, PROGNOSIS, AND MONITORING OF IMMUNE DISORDERS USING GALECTIN-1

(75) Inventors: Margaret A. Shipp, Wellesley, MA (US); Przemyslaw Juszczynski, Jamaica Plain, MA (US); Jing Ouyang, Chestnut Hill, MA (US); Jeffery Kutok, Natick, MA (US); Scott Rodig, Westwood, MA (US); Gabriel Rabinovich, Ciudad de Buenos Aires (AR)

(73) Assignees: Dana-Farber Cancer Institute, Inc., Boston, MA (US); Consejo Nactional De Investigaciones Cientificias Y Tecnicas, Buenos Aires (AR); Fundacion Sales, Buenos Aires (AR)

( * ) Notice: Subject to any disclaimer, the term of this patent is extended or adjusted under 35 U.S.C. 154(b) by 197 days.

(21) Appl. No.: 12/175,249

(22) Filed: Jul. 17, 2008

(65) Prior Publication Data
US 2009/0176223 A1 Jul. 9, 2009

Related U.S. Application Data

(60) Provisional application No. 60/959,830, filed on Jul. 17, 2007, provisional application No. 61/003,254, filed on Nov. 15, 2007.

(51) Int. Cl.
| | | |
|---|---|---|
| *G01N 33/53* | (2006.01) | |
| *G01N 33/68* | (2006.01) | |
| *G01N 33/574* | (2006.01) | |
| *A61K 39/395* | (2006.01) | |
| *G01N 33/50* | (2006.01) | |

(52) U.S. Cl.
CPC ....... *G01N 33/5052* (2013.01); *A61K 39/395* (2013.01); *G01N 33/574* (2013.01); *G01N 33/57426* (2013.01); *G01N 33/57488* (2013.01); *G01N 2333/4724* (2013.01); *G01N 2800/52* (2013.01); *G01N 2800/56* (2013.01); *Y10T 436/105831* (2015.01)

(58) Field of Classification Search
CPC .......... A61K 39/0011; A61K 2039/505; A61K 38/1709; A61K 39/39558; A61K 51/1045; C07K 2316/96; C07K 14/47; C07K 16/00
See application file for complete search history.

(56) References Cited

U.S. PATENT DOCUMENTS

| | | | |
|---|---|---|---|
| 7,011,947 B2 * | 3/2006 | Golub et al. ............... | 435/6.14 |
| 2002/0006404 A1 | 1/2002 | Hanna et al. | |
| 2003/0109464 A1 * | 6/2003 | Huflejt et al. ............. | 514/42 |
| 2004/0023855 A1 | 2/2004 | John et al. | |
| 2007/0207161 A1 | 9/2007 | Ralph | |

FOREIGN PATENT DOCUMENTS

| | | |
|---|---|---|
| WO | WO-99/12041 | 3/1999 |
| WO | WO-2004/030615 | 4/2004 |
| WO | WO-2006/108474 | 10/2006 |
| WO | WO-2007/013807 | 2/2007 |

OTHER PUBLICATIONS

Le et al., J. Clin. Oncol., 2005, vol. 23(35):8932-8941.*
He et al., J. Biol. Chem., 2004, vol. 279(6):4705-4712.*
D'Haene et al., Int. J. Immunopathol. Pharmacol., 2005, vol. 18(3):431-443.*
Gajl-Peczalska et al., Am. J. Med., 1975, vol. 59(5):674-685 (Abstract).*
Cho et al., J. Biol. Chem., 1995, vol. 270:5198-5206.*
Williams et al., British Journal of Haematology, 2002, vol. 117:812-820.*
Rodig et al., Clin. Cancer Res., 2008, vol. 14(11):3338-3344.*
Abramson et al., "Advances in the biology and therapy of diffuse large B-cell lymphoma: moving toward a molecularly targeted approach," Blood, 106(4):1154-1174 (2005).
Amano et al., "The ST6Gal I Sialyltransferase Selectively Modifies N-Glycans on CD45 to Negatively Regulate Galectin-1-induced CD45 Clustering, Phosphatase Modulation, and T Cell Death," Journal of Biological Chemistry, 278(9):7469-7475 (2003).
Armstrong et al., "MLL translocations specify a distinct gene expression profile that distinguishes a unique leukemia," Nat. Genet., 30(1):41-47 (2002).
Baum et al., "Amelioration of graft versus host disease by galectin-1," Clin. Immunol., 109(3):295-307 (2003).
Benjamini et al., "Controlling the false discovery rate in behavior genetics research," Behav. Brain Res., 125(1-2):279-284 (2001).
Camby et al., "Galectin-1 modulates human glioblastoma cell migration into the brain through modifications to the actin cytoskeleton and levels of expression of small GTPases," J. Neuropathol. Exp. Neurol., 61(7):585-596 (2002).
Camby et al., "Galectin-1: a small protein with major functions," Glycobiology, 16(11):137R-157R (2006).
Derijard et al., "JNK1: a protein kinase stimulated by UV light and Ha-Ras that binds and phosphorylates the c-Jun activation domain," Cell, 76(6):1025-1037 (1994).
Drakos et al., "c-Jun expression and activation are restricted to CD30+ lymphoproliferative disorders," Am. J. Surg. Pathol., 31(3):447-453 (2007).
Gabrilovich, D.I., "Molecular mechanisms and therapeutic reversal of immune suppression in cancer," Curr. Cancer Drug Targets, 7(1):1 (2007).
Gandhi et al., "Expression of LAG-3 by tumor-infiltrating lymphocytes is coincident with the suppression of latent membrane antigen-specific CD8+ T-cell function in Hodgkin lymphoma patients," Blood, 108(7):2280-2289 (2006).
Gandhi et al., "Galectin-1 mediated suppression of Epstein-Barr virus-specific T-cell immunity in classic Hodgkin lymphoma," Blood, 110(4):1326-1329 (2007).
He et al., "Presentation of Galectin-1 by Extracellular Matrix Triggers T Cell Death," Journal of Biological Chemistry, 279(6):4705-4712 (2004).

(Continued)

*Primary Examiner* — Xiaozhen Xie
(74) *Attorney, Agent, or Firm* — Foley Hoag LLP

(57) ABSTRACT

The present invention is based, in part, on the discovery that galectin-1 (Gal1) plays a role in immune disorders, including Hodgkin lymphoma, anaplastic large cell lymphoma, or MLL+ pre B-cell ALL. Accordingly, the invention relates to compositions, kits, and methods for diagnosing, prognosing, and monitoring immune disorders, e.g., Hodgkin lymphoma, anaplastic large cell lymphoma, or MLL+ pre B-cell ALL.

16 Claims, 6 Drawing Sheets

(56) References Cited

OTHER PUBLICATIONS

Ishida et al., "Specific Recruitment of CC Chemokine Receptor 4-Positive Regulatory T Cells in Hodgkin Lymphoma Fosters Immune Privilege," Cancer Research, 66(11):5716-5722 (2006).

Jenner et al., "Increased alpha2,6-siaylation of surface proteins on tolerogenic, immature dendritic cells and regulatory T cells," Exp. Hematol., 34(9):1212-1218 (2006).

Juszcynski et al., "BAL1 and BBAP Are Regulated by a Gamma Interferon-Responsive Bidirectional Promoter and Are Overexpressed in Diffiuse Large B-Cell Lymphomas with a Prominent Inflammatory Infiltrate," Molecular and Cellular Biology, 26(14):5348-5359 (2006).

Juszczynski, P., "Hodgkin's Lymphoma Reed Sternberg Cells Over Express the T-cell Inhibitory Carbohydrate-binding Lectin, Galectin 1: Role of AP-1 and Likely Mechanism of Tumor Immune Escape," Abstract for Presentation at the 48th ASH Annual Meeting, Orlando, Florida, Dec. 9-12, 2006.

Kanzler et al., "Hodgkin and Reed-Sternberg Cells in Hodgkin's Disease Represent the Outgrowth of a Dominant Tumor Clone Derived from (Crippled) Germinal Center B Cells," J. Exp. Med., 184:1495-1505 (1996).

Kuppers et al., "Biology of Hodgkin's lymphoma," Ann. Oncol., 13 Suppl 1:11-18 (2002).

Le et al., "Galectin-1: a link between tumor hypoxia and tumor immune privilege," J. Clin. Oncol., 23(35):8932-8941 (2005).

Liu et al., "Galectins as modulators of tumour progression," Nat. Rev. Cancer, 5(1):29-41 (2005).

Loots et al., "rVISTA 2.0: evolutionary analysis of transcription factor binding sites," Nucleic Acids Research, 32:W217-W221 (2004).

Ludes-Meyers et al., "AP-1 blockade inhibits the growth of normal and malignant breast cells," Oncogene, 20:2771-2780 (2001).

Marshall et al., "Immunosuppressive regulatory T cells are abundant in the reactive lymphocytes of Hodgkin lymphoma," Blood, 103(5):1755-1762 (2004).

Mathas et al., "Aberrantly expressed c-Jun and JunB are a hallmark of Hodgkin lymphoma cells, stimulate proliferation and synergize with NF-κB," European Molecular Biology Organization Journal, 21:4104-4113 (2002).

Monti et al., "Molecular profiling of diffuse large B-cell lymphoma identifies robust subtypes including one characterized by host inflammatory response," Blood, 105(5):1851-1861 (2005).

Perillo et al., "Apoptosis of T cells mediated by galectin-1," Nature, 378:(6558)736-739 (1995).

Polo et al., "Transcriptional signature with differential expression of BCL6 target genes accurately identifies BCL6-dependent diffuse large B cell lymphomas," PNAS, 104(9):3207-3212 (2007).

Rabinovich, GA, "Galectin-1 as a potential cancer target," British Journal of Cancer, 92:1188-1192 (2005).

Rabinovich et al., "Galectins and their ligands: amplifiers, silencers or tuners of the inflammatory response?," Trends Immunol., 23(6):313-320 (2002).

Rabinovich et al., "Recombinant Galectin-1 and Its Genetic Delivery Suppress Collagen-induced Arthritis via T Cell Apoptosis," J. Exp. Med., 190(3):385-397 (1999).

Re et al., "Molecular pathogenesis of Hodgkin's lymphoma," J. Clin. Oncol., 23(26):6379-6386 (2005).

Reiner et al., "Identifying differentially expressed genes using false discovery rate controlling procedures," Bioinformatics, 19(3):368-375 (2003).

Rodig et al., "TRAF1 expression and c-Rel activation are useful adjuncts in distinguishing classical Hodgkin lymphoma from a subset of morphologically or immunophenotypically similar lymphomas," Am. J. Surg. Pathol., 29(2):196-203 (2005).

Rubinstein et al., "Targeted inhibition of galectin-1 gene expression in tumor cells results in heightened T cell-mediated rejection; A potential mechanism of tumor-immune privilege," Cancer Cell, 5(3):241-251 (2004).

Salvatore et al., "High resolution methylation analysis of the galectin-1 gene promoter region in expressing and nonexpressing tissues," FEBS Lett., 421(2):152-158 (1998).

Santucci et al., "Galectin-1 suppresses experimental colitis in mice," Gastroenterology, 124(5):1381-1394 (2003).

Savage et al., "The molecular signature of mediastinal large B-cell lymphoma differs from that of other diffuse large B-cell lymphomas and shares features with classical Hodgkin lymphoma," Blood, 102(12):3871-3879 (2003).

Scherf et al., "Highly specific localization of promoter regions in large genomic sequences by Promoterinspector: a novel context analysis approach," J. Mol. Biol., 297(3):599-606 (2000).

Schwering et al., "Loss of the B-lineage-specific gene expression program in Hodgkin and Reed-Sternberg cells of Hodgkin lymphoma," Blood, 101(4):1505-1512 (2003).

Skinnider et al., "The role of interleukin 13 in classical Hodgkin lymphoma," Leuk. Lymphoma, 43(6):1203-1210 (2002).

Smith et al., "The phosphodiesterase PDE4B limits cAMP-associated PI3K/AKT-dependent apoptosis in diffuse large B-cell lymphoma," Blood, 105(1):308-316 (2005).

Stillman et al., "Galectin-3 and Galectin-1 Bind Distinct Cell Surface Glycoprotein Receptors to Induce T Cell Death," The Journal of Immunology, 176:778-789 (2006).

Thijssen et al., "Galectic-1 is essential in tumor angiogenesis and is a target for antiangiogenesis therapy," PNAS, 103(43):15975-15980 (2006).

Toscano et al., "Differential glycosylation of TH1, TH2 and TH-17 effector cells selectively regulates susceptibility to cell death," Nat. Immunol., 8(8):825-834 (2007).

Toscano et al., "Dissecting the pathophysiologic role of endogeneous lectins: glycan-binding proteins with cytokine-like activity?," Cytokine Growth Factor Rev., 18(1-2):57-71 (2007).

Toscano et al., "Galectin-1 Suppresses Autoimmune Retinal Disease by Promoting Concomitant Th2- and T Regulatory-Mediated Anti-Inflammatory Response," The Journal of Immunology, 176:6323-6332 (2006).

van der Leij et al., "Strongly enhanced IL-10 production using stable galectin-1 homodimers," Mol. Immunol., 44:506-513 (2007).

Vasta et al., "Structural and functional diversity of lectin repertoires in invertebrates, protochordates and ectothermic vertebrates," Curr. Opin. Struct. Biol., 14(5):617-630 (2004).

von Wasielewski et al., "Tissue eosinophilia correlates strongly with poor prognosis in nodular sclerosing Hodgkin's disease, allowing for known prognostic factors," Blood, 95(4):1207-1213 (2000).

Yuan et al., "siRNA Selection Server: an automated siRNA oligonucleotide prediction server," Nucleic Acids Research, 32:W130-W134 (2004).

Zorn et al., "IL-2 regulates FOXP3 expression in human CD4+CD25+ regulatory T cells through a STAT-dependent mechanism and induces the expansion of these cells in vivo," Blood, 108(5):1571-1579 (2006).

Baum et al., "Human Thymic Epithelial Cells Express an Endogenous Lectin, Galectin-1, which Binds to Core 2 O-Glycans on Thymocytes and T Lymphoblastoid Cells," Journal of Experimental Medicine, 181(3):877-887 (1995).

Cornillot et al., "Production and characterization of a monoclonal antibody able to discriminate galectin-1 from galectin-2 and galectin-3," Glycobiology, 8(5):425-432 (1998).

D'Haene et al., "The Differential Expression of Galectin-1 and Galectin-3 in Normal Lymphoid Tissue and Non-Hodgkin's and Hodgkin's Lymphomas," International Journal of Immunopathology and Pharmacology, 18(3):431-443 (2005).

Gabius et al., "Association of Galectin-1- but not Galectin-3-dependent Parameters with Proliferation Activity in Human Neuroblastomas and Small Cell Lung Carcinomas," Anticancer Research, 22(1A):407-408 (2002).

Giguere et al., "Carbohydrate triazoles and isoxazoles as inhibitors of galectins-1 and -3," Chemical Communications, pp. 2379-2381 (2006).

Juszczunski et al., "The AP1-dependent secretion of galectin-1 by Reed-Sternberg cells fosters immune privilege in classical Hodgkin lymphoma," Proceedings of the National Academy of Sciences, USA, 104(32):13134-13139 (2007).

(56) References Cited

OTHER PUBLICATIONS

La et al., "A Novel Biological Activity for Galectin-1," American Journal of Pathology, 163(4):1505-1515 (2003).

van den Brule, "Galectin-1 Modulates Human Melanoma Cell Adhesion to Laminin," Biochemical and Biophysical Research Communications, 209(2):760-767 (1995).

International Search Report dated Jan. 16, 2009 from PCT/US2008/070324.

Fluck et al., "Low-dose cyclophosphamide modulates galectin-1 expression and function in an experimental rat lymphoma model," Cancer Immunology, 56(2):237-248 (2006).

Garin et al., "Galectin-1: a key effector of regulation mediated by CD4+CD25+ T cells," Blood, 109(5):2058-2065 (2007).

Rodig et al., "AP1-Dependent Galectin-1 Expression Delineates Classical Hodgkin and Anaplastic Large Cell Lymphomas from Other Lymphoid Malignancies with Shared Molecular Features," Clinical Cancer Research, 24(11):3338-3344 (2008).

Rubenstein et al., "Targeted inhibition of galectin-1 gene expression in tumor cells results in heightened T cell-mediated rejection: A potential mechanism of tumor-immune privilege," Cancer Cell, 5(3):241-251 (2004).

Salvatore et al., "Galectin-1 gene expression and methylation state in human T leukemia cell lines," International Journal of Oncology, 17(5):1015-1018 (2000).

Velders et al., "Prospects for immunotherapy of acute lymphoblastic leukemia," Leukemia, 15(5):701-706 (2001).

International Search Report dated Jan. 27, 2009 from PCT/US2008/070328.

Elola et al., "Galectin-1 receptors in different cell types," Journal of Biomedical Science, 12:13-29 (2005).

Pei et al., "On the art of identifying effective and specific siRNAs," Nature Methods, 3(9):670-676 (2006).

Seth et al., "Delivery and biodistribution of siRNA for cancer therapy: challenges and future prospects," Ther. Deliv., 3(2):245-261 (2012).

Rush et al., "Primary Anaplastic Large Cell Lymphoma of the Lung: A Clinicopathologic Study of Five Patients," Med. Pathology, 13(12):1285-1292 (2000).

\* cited by examiner

SEQUENCE LISTING

```
<160> NUMBER OF SEQ ID NOS: 10

<210> SEQ ID NO 1
<211> LENGTH: 408
<212> TYPE: DNA
<213> ORGANISM: Homo sapiens

<400> SEQUENCE: 1
atggcttgtg gtctggtcgc cagcaacctg aatctcaaac ctggagagtg ccttcgagtg      60
cgaggcgagg tggctcctga cgctaagagc ttcgtgctga acctgggcaa agacagcaac     120
aacctgtgcc tgcacttcaa ccctcgcttc aacgcccacg gcgacgccaa caccatcgtg     180
tgcaacagca aggacggcgg ggcctggggg accgagcagc gggaggctgt ctttcccttc     240
cagcctggaa gtgttgcaga ggtgtgcatc accttcgacc aggccaacct gaccgtcaag     300
ctgccagatg gatacgaatt caagttcccc aaccgcctca acctggaggc catcaactac     360
atggcagctg acggtgactt caagatcaaa tgtgtggcct ttgactga                  408

<210> SEQ ID NO 2
<211> LENGTH: 135
```

-continued

```
<212> TYPE: PRT
<213> ORGANISM: Homo sapiens

<400> SEQUENCE: 2

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caagaattcc cagaacacgc tgcccagcgt c                                31

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaatctagag tcgcaacttg tcaagttctc aagtctgtc                        39

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttttctgggt gactcacttc ccccg                                       25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 6
ttttctgggt tcagtacttc ccccg                                           25

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gattccaccc atggcaaatt c                                               21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgattttgga gggatctcgc tc                                              22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcgccagcaa cctgaatctc                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcacgaagct cttagcgtca                                                 20
```

COMPOSITIONS, KITS, AND METHODS FOR THE DIAGNOSIS, PROGNOSIS, AND MONITORING OF IMMUNE DISORDERS USING GALECTIN-1

RELATED APPLICATIONS

This application claims the benefit of U.S. Provisional Application Ser. No. 60/959,830, filed on Jul. 17, 2007 and of U.S. Provisional Application Ser. No. 61/003,254, filed on Nov. 15, 2007; the entire contents of each of the applications is incorporated herein by reference.

BACKGROUND OF THE INVENTION

Classical Hodgkin lymphoma (cHL) is a B-cell malignancy diagnosed in approximately 20,000 new patients in North America and Europe each year; over 90% of these patients are young adults. Classical HLs include small numbers of malignant Reed-Sternberg (RS) cells within an extensive inflammatory infiltrate (Re et al. (2005) *J Clin Oncol* 23:6379-6386) which includes abundant T helper (Th)-2 and T regulatory ($T_{reg}$) cells. The tumor cells derive from pre-apoptotic germinal center B cells that have undergone crippling mutations of their rearranged immunoglobulin genes (Re et al. (2005) *J Clin Oncol* 23:6379-6386; Kanzler et al. (1996) *J Exp Med* 184:1495-1505). Classical HL RS cells lack B-cell receptor-mediated signals and rely on alternative survival and proliferation pathways activated by transcription factors such as NF-κB and AP1 (Mathas et al. (2002) *EMBO J.* 21: 4104-4113; Kuppers et al. (2002) *Ann Oncol* 13:11-18; Schwering et al. (2003) *Blood* 101: 1505-1512). In cHL, the tumor cells exhibit constitutive AP1 activation, express high levels of the AP1 components, cJUN and JUNB, and depend upon AP1-mediated proliferation signals (Mathas et al. (2002) *EMBO J.* 21: 4104-4113).

Although primary cHLs have a brisk inflammatory infiltrate, there is little evidence of an effective host anti-tumor immune response. The reactive T-cell population includes predominantly Th2-type and $CD4^+$ $CD25^{high}$ $FOXP3^+$ $T_{reg}$ cells that directly suppress immune responses and protect cHL RS cells from immune attack (Re et al. (2005) *J Clin Oncol* 23:6379-6386; Marshall et al. (2004) *Blood* 103: 1755-1762; Gandhi et al. (2006) *Blood* 108:2280-2289; Ishida et al. (2006) *Cancer Res* 66:5716-5722); Th1, NK and cytotoxic T cells are markedly under-represented. In addition, primary cHLs are characterized by a unique cytokine and chemokine profile, including IL-4, IL-5, IL-10 and IL-13 (Re et al. (2005) *J Clin Oncol* 23:6379-6386; Skinnider et al. (2002) *Leuk Lymphoma* 43:1203-1210). In fact, IL-13 is a critical growth factor for cHL RS cells (Re et al. (2005) *J Clin Oncol* 23:6379-6386; Skinnider et al. (2002) *Leuk Lymphoma* 43:1203-1210). However, the molecular signals and endogenous factors responsible for creating and maintaining the Th2-skewed immunosuppressive microenvironment in cHL remain to be defined.

Galectins have recently emerged as novel regulators of immune cell homeostasis, and tumor immune escape (Rabinovich et al. (2002) *Trends Immunol* 23:313-320; Liu and Rabinovich (2005) *Nature Reviews Cancer* 5:29-41; Rubinstein et al. (2004) *Cancer Cell* 5:241-251; Le et al. (2005) *J Clin Oncol* 23:8932-8941). Galectin-1 (Gal1), an evolutionarily conserved member of this family (Vasta et al. (2004) *Curr Opin Struct Biol* 14:617-630), preferentially recognizes multiple Gal β1,4 GlcNAc (LacNAc) units which may be presented on the branches of N- or O-linked glycans on cell surface glycoproteins such as CD45, CD43 and CD7 (Stillman et al. (2006) *J Immunol* 176:778-789). Through binding and crosslinking of specific glycoconjugates, Gal1 has the potential to inhibit T-cell effector functions and regulate the inflammatory response (Perillo et al. (1995) *Nature* 378:736-739; Rabinovich et al. (1999) *J Exp Med* 190:385-397; Toscano et al. (2006) *J Immunol* 176:6323-6332; Santucci et al. (2003) *Gastroenterol* 124: 1381-1394; Baum et al. (2003) *Clin Immunol* 109:295-307). In several murine models of chronic inflammatory diseases, recombinant Gal1 suppressed Th1-dependent responses and increased T-cell susceptibility to activation-induced cell death (Rabinovich et al. (1999) *J Exp Med* 190:385-397; Toscano et al. (2006) *J Immunol* 176:6323-6332; Santucci et al. (2003) *Gastroenterol* 124: 1381-1394; Baum et al. (2003) *Clin Immunol* 109:295-307).

In a recently described solid tumor (murine melanoma) model, Gal1 was also found to play a pivotal role in promoting escape from T-cell-dependent immunity and conferring immune privilege to tumor cells (Rubinstein et al. (2004) *Cancer Cell* 5:241-251). In this model, Gal1 blockade markedly enhanced syngeneic tumor rejection and tumor-specific T-cell-mediated immune responses (Rubinstein et al. (2004) *Cancer Cell* 5:241-251). In another recently described solid tumor (head and neck squamous cell carcinomas), Gal1 overexpression was inversely correlated with the number of infiltrating T cells and was an independent prognostic factor for shorter overall survival (Le et al. (2005) *J Clin Oncol* 23:8932-8941).

In view of the above, it is clear that there remains a need in the art for compositions and methods to combat immune disorders, including Hodgkin lymphoma, anaplastic large cell lymphoma, and $MLL^+$ pre B-cell ALL. The present invention relates in general to a role of Gal1 in immune disorders, including Hodgkin lymphoma, anaplastic large cell lymphoma, and $MLL^+$ pre B-cell ALL.

SUMMARY OF THE INVENTION

The present invention is based, in part, on the discovery that galectin-1 (Gal1) plays a role in immune disorders, including Hodgkin lymphoma, anaplastic large cell lymphoma, and pre B-cell acute lymphoblastic leukemia bearing an MLL gene translocation ($MLL^+$ pre B-cell ALL). Accordingly, in one aspect, the invention features a method for detecting a Gal1 polypeptide or nucleic acid or fragments thereof in a sample. In one embodiment, the method includes contacting the sample with a compound which selectively binds to a Gal1 polypeptide or fragment thereof and determining whether the compound binds to a Gal1 polypeptide or fragment thereof in the sample to thereby detect the presence of a Gal1 polypeptide or fragment thereof. In one embodiment, the compound which binds to the polypeptide is an antibody. In another aspect, the method includes contacting a sample with a nucleic acid probe or primer which selectively hybridizes to a Gal1 polynucleotide or fragment thereof and determining whether the nucleic acid probe or primer binds to a nucleic acid molecule in the sample to thereby detect the presence of a Gal1 polynucleotide or fragment thereof. In yet another embodiment, the sample comprises mRNA molecules and is contacted with a nucleic acid probe.

In yet another aspect, the invention provides a method for identifying a compound which binds to a Gal1 polypeptide or fragment thereof. In one such embodiment, the method includes contacting a Gal1 polypeptide or fragment thereof, or a cell expressing said polypeptide with a test compound and determining whether said polypeptide binds to the test compound. In another embodiment, the binding of the test compound to a Gal1 polypeptide or fragment thereof is detected by several methods, including detection of binding by direct detection of test compound/polypeptide binding, detection of binding using a competition binding assay, and detection of binding using an assay for Gal1 activity.

In one aspect, the invention provides for a method of assessing whether a subject has a condition, e.g., an immune disorder, including cancer, e.g., Hodgkin lymphoma, anaplastic large cell lymphoma, or MLL$^+$ pre B-cell ALL, that would benefit from upregulation of an immune response. In one embodiment, the method includes comparing the level of expression of Gal1 in a subject sample and the normal level of expression of Gal1 in a control sample, wherein a significant increase in the level of expression of Gal1 in the subject sample relative to the normal level is an indication that the subject is afflicted with a condition. In another embodiment, the sample comprises cells obtained from the subject, for example, cells in fluid (e.g., whole blood fluid, serum fluid, plasma fluid, interstitial fluid, cerebrospinal fluid, lymph fluid, saliva, stool, and urine). In another embodiment, the level of expression of Gal1 is assessed by detecting the presence in the samples of a protein encoded by a Gal1 polynucleotide or a polypeptide or protein fragment thereof comprising the protein. For example, the presence of the protein can be detected using a reagent which specifically binds to the protein, e.g., an antibody, an antibody derivative, or an antibody fragment. In another embodiment, the level of expression of Gal1 is assessed by detecting the presence in the sample of a transcribed polynucleotide encoded by a Gal1 polynucleotide or a portion of the transcribed polynucleotide, e.g., mRNA or cDNA. For example, the presence of the polynucleotide can be assayed by detecting the presence in the sample of a transcribed polynucleotide which anneals with a Gal1 polynucleotide or anneals with a portion of a Gal1 polynucleotide, under stringent hybridization conditions. In another embodiment, the transcribed polynucleotide to be detected can be amplified. In still another embodiment, a significant increase between the level of expression of Gal1 in the subject sample relative to the normal level of expression of Gal1 in the sample from the control subject can be at least about two, three, four, five, six, seven, eight, nine, ten, twenty or more fold greater.

In another aspect, the invention provides for a method for monitoring the progression of an immune disorder, e.g., Hodgkin lymphoma, anaplastic large cell lymphoma, or MLL$^+$ pre B-cell ALL, in a subject. In one embodiment, the method includes detecting in a subject sample at a first point in time the expression of Gal1, repeating the previous step at a subsequent point in time, and comparing the level of expression of Gal1 detected at each point in time to monitor the progression of the immune disorder. In another embodiment, the subject can undergo treatment to ameliorate the immune disorder between the first point in time and the subsequent point in time. In one embodiment, the treatment may be chemotherapy. In yet another embodiment, the chemotherapy treatment may be combined with an agent.

In another aspect, the invention provides for a method for assessing the efficacy of a test compound for inhibiting an immune disorder, e.g., Hodgkin lymphoma, anaplastic large cell lymphoma, or MLL$^+$ pre B-cell ALL, in a subject. In one embodiment, the method includes comparing the level of expression of Gal1 in a first sample obtained from the subject and exposed to the test compound and the level of expression of Gal1 in a second sample obtained from the subject, wherein the second sample is not exposed to the test compound, and a significantly lower level of expression of Gal1, relative to the second sample, is an indication that the test compound is efficacious for inhibiting an immune disorder in the subject. In another embodiment, the first and second samples can be portions of a single sample obtained from the subject or portions of pooled samples obtained from the subject. In yet another embodiment, the method further comprises administering a combination treatment, wherein the treatment may include chemotherapy.

In another aspect, the invention provides for a method for predicting the clinical outcome of a patient with an immune disorder, e.g., Hodgkin lymphoma, anaplastic large cell lymphoma, or MLL$^+$ pre B-cell ALL. In one embodiment, the method includes determining the level of expression of Gal1 in a patient sample, determining the level of expression of Gal1 in a sample from a control subject having a good clinical outcome, and comparing the level of expression of Gal1 in the patient sample and in the sample from the control subject, wherein a significantly higher level of expression in the patient sample as compared to the expression level in the sample from the control subject is an indication that the patient has a poor clinical outcome.

In another aspect, the invention provides for a method of assessing the efficacy of a therapy for inhibiting an immune disorder, e.g., Hodgkin lymphoma, anaplastic large cell lymphoma, or MLL$^+$ pre B-cell ALL, in a subject. In one embodiment, the method includes comparing the level of expression of Gal1 in the first sample obtained from the subject prior to providing at least a portion of the therapy to the subject and the level of expression of Gal1 in a second sample obtained from the subject following provision of the portion of the therapy, wherein a significantly lower level of expression of Gal1 in the second sample, relative to the first sample, is an indication that the therapy is efficacious for inhibiting the immune disorder, e.g., Hodgkin lymphoma, anaplastic large cell lymphoma, or MLL$^+$ pre B-cell ALL, in the subject.

In another aspect, the invention provides for methods of making antibodies that specifically bind to a Gal1 polypeptide or a fragment thereof. In one embodiment, the method involves making an isolated hybridoma and includes immunizing a mammal using a composition comprising a Gal1 polypeptide or a fragment thereof, isolating splenocytes from the immunized mammal, fusing the isolated splenocytes with an immortalized cell line to form hybridomas, and screening individual hybridomas for production of an antibody which specifically binds with the polypeptide thereof to isolate the hybridoma. In another embodiment, the antibody or antigen binding fragment thereof produced by the hybridoma can be used to specifically recognize Gal1 polypeptide or a fragment thereof. In still another embodiment, antibodies that specifically bind to a Gal1 polypeptide or a fragment thereof can be made by immunizing a mammal with an effective amount of a preparation of a material comprising a Gal1 polypeptide or a fragment thereof, in combination with an adjuvant.

In another aspect, the invention provides for novel compositions of matter that may be used in the methods of the invention. In one embodiment, the invention provides antibodies or antigen binding fragment thereof that specifically bind to a Gal1 polypeptide or a fragment thereof. In one embodiment, the antibodies or antigen binding fragment thereof can bind to a fragment of human Gal1, a polypeptide which is encoded by a nucleic acid comprising a nucleotide sequence which is at least 80% homologous to a nucleic acid comprising the nucleotide sequence human Gal1, or a polypeptide comprising an amino acid sequence which is at least 80% homologous to the amino acid sequence of human Gal1. In other embodiments, the antibodies or antigen binding portions thereof can be monoclonal, polyclonal, chimeric, or humanized. In another embodiment, the antibodies or antigen binding portions thereof can be detectably labeled. Non-limiting examples of detectable labels include an enzyme, a prosthetic group, a fluorescent material, a luminescent material, a bioluminescent material, and a radioactive material. In other embodiments, the antibodies or antigen binding portions thereof inhibit Hodgkin lymphoma, anaplastic large cell lymphoma, or MLL$^+$ pre B-cell ALL in a subject. In yet another embodiment, the antibodies or antigen binding portions thereof specifically bind a Gal1 epitope comprising the ligand-specific carbohydrate binding domain or fragments thereof, e.g., amino acids 30 to 90 of human Gal1 or amino acids 62 to 86 of human Gal1. In another embodiment, the antibodies or antigen binding portion thereof can comprise an effector domain and/or an Fc domain. In yet another embodiment, the antibodies or antigen binding portion thereof can be single-chain antibodies and/or Fab fragments. In still another embodiment, a pharmaceutical composition comprising the antibodies or antigen binding portion thereof in a pharmaceutically acceptable carrier are provided.

In still another aspect, the invention provides for various kits, which may include the novel compositions described herein. In one embodiment, a kit is provided that comprises an agent which selectively binds to a Gal1 polypeptide or fragment thereof and instructions for use. In another embodiment, a kit is provided that comprises an agent which selectively hybridizes to a Gal1 polynucleotide or fragment thereof and instructions for use.

BRIEF DESCRIPTION OF THE DRAWINGS

In FIG. 1A, the Gal1 expression profiles of DLBCL, MLBCL and cHL cell lines are shown. The color scale at the bottom of the figure indicates relative expression and standard deviations from the mean. Red connotes high-level expression, while blue indicates low-level expression. In FIG. 1B, the plots represent the median expression of Gal1 (boxes) in LBCL versus cHL cell lines ±25-75 percentile (bars) and range (whiskers). In FIG. 1C, the respective cHL cell lines (KMHZ, HDLM2, SupHD1, L1236, L540, L428, HD-MY-Z), the MLBCL cell line (Karpas 1106) and DLBCL cell lines (all others) are indicated. FIG. 1D shows immunohistochemical (IHC) analyses of Gal1 in representative primary cHL (top panels) and DLBCL (bottom panels) cells (original magnification 40× and 400×, respectively).

FIG. 2A shows the results of analyses of the AP1-dependent Gal1 enhancer. The previously described Gal1 promoter (Salvatore et al. (1998) *FEBS Lett* 421:152-8) and putative enhancer element including or lacking the predicted AP1 binding site (represented by a black bar) were cloned into a luciferase reporter vector, transiently transfected into cHL HD-MY-Z cells and assayed for luciferase activities. Representative luciferase activities from three independent experiments were normalized to *Renilla* luciferase activity and presented as bars±standard deviations. FIG. 2B shows results of the selective activity of the Gal1 enhancer. Classical HL, DLBCL and fibroblast cell lines were transfected with either the Gal1 promoter-only vector (pGL3-Gal1$_{-403+67}$-Luc) or the promoter-enhancer construct (pGL3-Gal1$_{403+67}$-Luc-e$_{1346+1746}$) and assessed as in FIG. 2A for their respective luciferase activities. FIG. 2C shows that the Gal1 enhancer is dependent on AP-1 using electrophoretic mobility shift assays. Nuclear extracts from DLBCL cell lines (DHL4, DHL7 and Toledo) or cHL cell lines (HD-MY-Z, L428 and SupHD1) were incubated with wild type (WT) or mutant (MUT) $^{32}$P labeled, double-stranded DNA probe corresponding to an AP1 binding site in the Gal1 enhancer. Specific, unlabeled competitor and antibodies against cJun or β-actin (control) were included in certain assays as indicated. The gel-shift band corresponding to probe-protein complex is indicated with an arrow and supershift bands corresponding to probe-protein-antibody complex are noted with asterisks. FIG. 2D shows that the Gal1 enhancer is dependent on cJUN. HD-MY-Z cells were cotransfected with the Gal1 promoter-only vector or the Gal1 promoter-enhancer construct with either the dominant-negative cJUN (cJUN-DN) construct (cJUN-DN) or empty vector. Luciferase activities were determined as in FIG. 2A. FIG. 2E shows that inhibition of AP1 decreases Gal1 transcript abundance. HD-MY-Z cells were transfected with either the dominant-negative cJUN construct (cJUN-DN) or empty vector and relative Gal1 mRNA abundance was then assessed by RQ-PCR.

FIG. 4A shows CHL, with cytoplasmic staining scored as 3+ in the RS cells and variants. FIG. 4B shows CHL, with cytoplasmic staining scored as 2+ in the Reed-Sternberg cells and variants. FIG. 4C shows nodular lymphocyte-predominant Hodgkin lymphoma with weak, perinuclear staining of the L&H cells that was scored as negative. FIG. 4D shows primary mediastinal large B cell lymphoma with no cytoplasmic staining of tumor cells but cytoplasmic staining of an adjacent macrophage (arrow). FIG. 4E shows diffuse large B cell lymphoma with no cytoplasmic staining of tumor cells, but with weak cytoplasmic staining of an intermixed macrophage (arrow). FIG. 4F shows anaplastic large cell lymphoma with cytoplasmic staining of tumor cells scored as 3+.

DETAILED DESCRIPTION OF THE INVENTION

Figure 1:
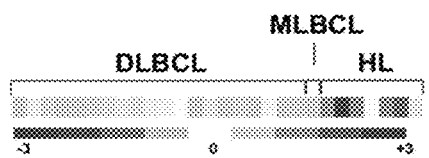
FIGS. 1A-1D shows that Gal1 is overexpressed in cHL cell lines and primary tumors. Relative Gal1 mRNA abundance (FIG. 1A and FIG. 1B) and protein expression (FIG. 1C) in a panel of LBCL and cHL cell lines is depicted.
Figure 1:
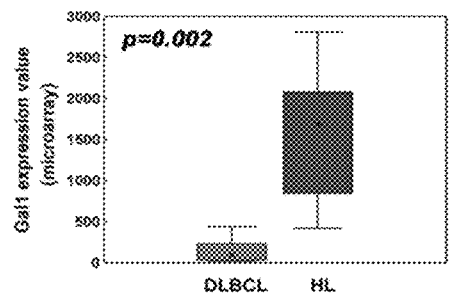
Figure 1:
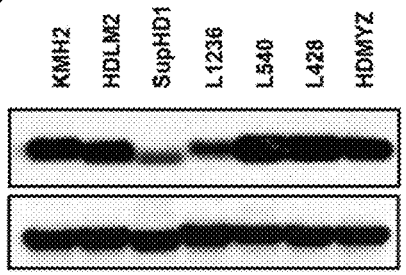
Figure 1:
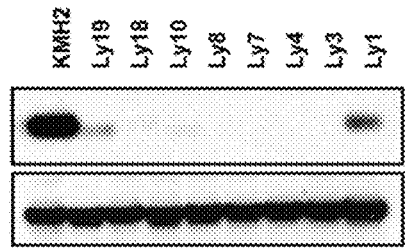
Figure 1:
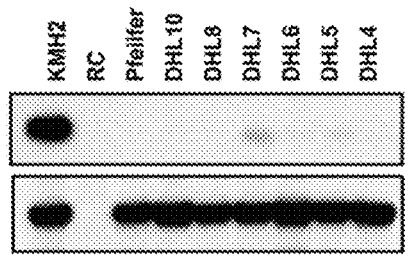
Figure 1:
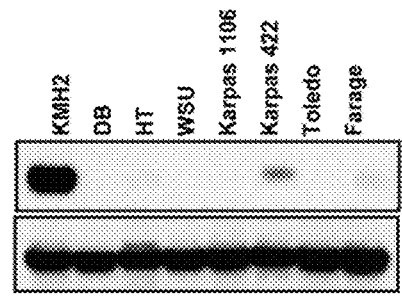
Figure 1:
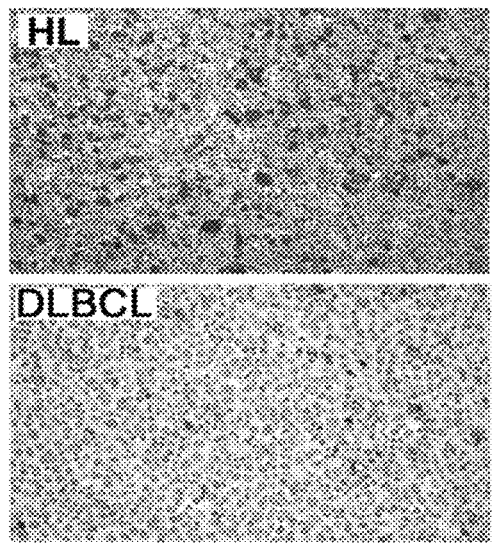
Figure 1:
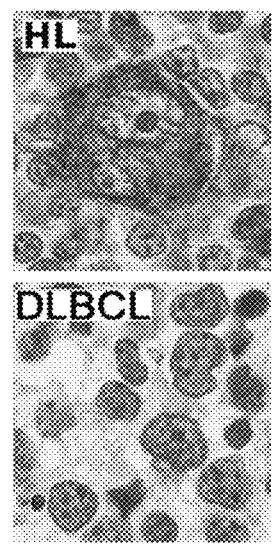

The invention is based, in part, on the discovery that galectin-1 (Gal1) is overexpressed by Reed-Sternberg (RS) cells associated with classical Hodgkin lymphomas (cHLs) and that the Gal1 overexpression by RS cells is directly implicated in the development and maintenance of an immunosuppressive Th2/T$_{reg}$-skewed microenvironment in cHL leading to an ineffective host anti-tumor immune response. Gal1 is also shown herein to delineate anaplastic large cell lymphoma (ALCL). In addition, it is shown herein that Gal1 expression is a highly sensitive and specific marker of pre B-cell acute lymphoblastic leukemia bearing an MLL gene translocation (MLL$^+$ pre B-cell ALL) which is particularly useful for diagnosis. Since MLL$^+$ pre B-cell ALL has a very poor prognosis, delineation of this leukemia subtype is particularly important.

Thus, it has been discovered that a higher than normal level of expression of Gal1 correlates with the presence of an immune disorder, e.g., Hodgkin lymphoma, anaplastic large cell lymphoma, or MLL$^+$ pre B-cell ALL, in a patient. Gal1 polypeptides and fragments thereof, e.g., biologically active or antigenic fragments thereof, are provided, as reagents or targets in assays applicable to diagnosis of immune disorders, e.g., Hodgkin lymphoma, anaplastic large cell lymphoma, or MLL$^+$ pre B-cell ALL. For example, Gal1 expression delineates at least Hodgkin lymphoma and anaplastic large cell lymphoma (ALCL), two aggressive B-cell lymphomas that are driven by constitutive AP-1 activity, as well as MLL$^+$ pre-B cell ALL, which is a subtype of pre-B cell acute lymphoblastic leukemia. In particular, the methods and compositions of the present invention relate to detection of expression and/or activity of a Gal1 gene or fragment thereof, e.g., biologically active fragments thereof, as well as to the detection of expression and/or activity of gene products or fragments thereof encoded by the Gal1 gene, e.g., biologically active fragments thereof. The methods and compositions of the present invention can utilize the Gal1 gene or gene sequence or fragments thereof, as well as gene products of the Gal1 gene and/or fragments thereof, e.g., antibodies which specifically bind to such Gal1 gene products.

In one aspect, methods are provided for detecting the presence, absence, stage, and other characteristics of immune disorders, e.g., Hodgkin lymphoma, anaplastic large cell lymphoma, or MLL$^+$ pre B-cell ALL, in a sample that are relevant to prognosis, diagnosis, monitoring, and characterization in a patient.

The invention also features compositions of matter, including antibodies (e.g., antibodies which specifically bind to any one of the polypeptides described herein) as well as fusion polypeptides, including all or a fragment of a polypeptide described herein.

I. Definitions

The articles "a" and "an" are used herein to refer to one or to more than one (i.e. to at least one) of the grammatical object of the article. By way of example, "an element" means one element or more than one element.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., Gal1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242: 423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to Gal1 polypeptides or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATT-GCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune disorder" includes immune diseases, conditions, and predispositions to, including, but not limited to, Hodgkin lymphoma (including, e.g., lymphocyte-rich classical Hodgkin lymphoma, mixed cellularity classical Hodgkin lymphoma, lymphocyte-depleted classical Hodgkin lymphoma, nodular sclerosis classical Hodgkin lymphoma, anaplastic large cell lymphoma, or MLL⁺ pre B-cell ALL, cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy).

As used herein, the term "immune response" includes T cell mediated and/or B cell mediated immune responses. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "inhibit" includes the decrease, limitation, or blockage, of, for example a particular action, function, or interaction.

As used herein, the term "interaction", when referring to an interaction between two molecules, refers to the physical contact (e.g., binding) of the molecules with one another. Generally, such an interaction results in an activity (which produces a biological effect) of one or both of said molecules.

An "isolated antibody", as used herein, is intended to refer to an antibody that is substantially free of other antibodies having different antigenic specificities (e.g., an isolated antibody that specifically binds Gal1 polypeptide or a fragment thereof is substantially free of antibodies that specifically bind antigens other than a Gal1 polypeptide or a fragment thereof). Moreover, an isolated antibody may be substantially free of other cellular material and/or chemicals.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of Gal1 polypeptide or fragment thereof, in which the protein is separated from cellular components of the cells from which it is isolated or recombinantly produced. In one embodiment, the language "substantially free of cellular material" includes preparations of Gal1 protein or fragment thereof, having less than about 30% (by dry weight) of non-Gal1 protein (also referred to herein as a "contaminating protein"), more preferably less than about 20% of non-Gal1 protein, still more preferably less than about 10% of non-Gal1 protein, and most preferably less than about 5% non-Gal1 protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe, for specifically detecting the expression of a marker of the invention. The kit may be promoted, distributed, or sold as a unit for performing the methods of the present invention.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the invention. A marker protein comprises the entire or a partial sequence of any of the sequences set forth in the Sequence Listing. The terms "protein" and "polypeptide" are used interchangeably.

The "normal" level of expression of a marker is the level of expression of the marker in cells of a subject, e.g., a human patient, not afflicted with an immune disorder, e.g., Hodgkin lymphoma, anaplastic large cell lymphoma, or MLL⁺ pre B-cell ALL. An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples. A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, "subject" refers to any healthy animal, mammal or human, or any animal, mammal or human afflicted with an immune disorder, e.g., Hodgkin lymphoma, anaplastic large cell lymphoma, or MLL+ pre B-cell ALL. The term "subject" is interchangeable with "patient".

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

I. Description

The present invention relates to methods and compositions for the diagnosis, prognosis, and monitoring of immune disorders, especially T lymphocyte-related disorders, including, but not limited to, Hodgkin lymphoma (including, e.g., lymphocyte-rich classical Hodgkin lymphoma, mixed cellularity classical Hodgkin lymphoma, lymphocyte-depleted classical Hodgkin lymphoma, nodular sclerosis classical Hodgkin lymphoma, anaplastic large cell lymphoma, or MLL$^+$ pre B-cell ALL cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy).

In particular, the methods and compositions of the present invention relate to detection of expression and/or activity of a gene referred to herein as the Gal1 gene or a fragment thereof, e.g., a biologically active fragment thereof, as well as to the detection of expression and/or activity of gene products encoded by the Gal1 gene (i.e., a "Gal1 gene product") or fragments thereof, e.g., biologically active fragments thereof. The methods and compositions of the present invention can utilize the Gal1 gene or gene sequence or fragments thereof, as well as gene products of the Gal1 gene, e.g., antibodies which specifically bind to such Gal1 gene products, or fragments thereof. Sequences, structures, domains, biophysical characteristics, and functions of Gal1 gene and gene products have been described in the art. See, for example, Rabinovich et al. (2002) *Trends Immunol* 23:313-320; Liu and Rabinovich (2005) *Nature Reviews Cancer* 5:29-41; Rubinstein et al. (2004) *Cancer Cell* 5:241-251; Le et al. (2005) *J Clin Oncol* 23:8932-8941; Vasta et al. (2004) *Curr Opin Struct Biol* 14:617-630; Toscano et al. (2007) *Cyt Growth Fact Rev* 18:57-71; Camby et al. (2006) *Glycobiol* 16:137R-157R, each of which is incorporated herein, by reference, in its entirety. Gal1 gene and gene products from many species are known and include, for example, chimpanzee Gal1 (NCBI Accession XM_001162066), rat Gal1 (NCBI Accession NM_019904), mouse Gal1 (NM_008495), and chicken Gal1 (NM_205495). Human Gal1 sequences include those listed below.

```
Gal1 coding nucleic acid sequence (SEQ ID NO: 1):
ATGGCTTGTG GTCTGGTCGC CAGCAACCTG AATCTCAAAC

CTGGAGAGTG CCTTCGAGTG CGAGGCGAGG TGGCTCCTGA

CGCTAAGAGC TTCGTGCTGA ACCTGGGCAA AGACAGCAAC

AACCTGTGCC TGCACTTCAA CCCTCGCTTC AACGCCCACG

GCGACGCCAA CACCATCGTG TGCAACAGCA AGGACGGCGG

GGCCTGGGGG ACCGAGCAGC GGGAGGCTGT CTTTCCCTTC

CAGCCTGGAA GTGTTGCAGA GGTGTGCATC ACCTTCGACC

AGGCCAACCT GACCGTCAAG CTGCCAGATG GATACGAATT

CAAGTTCCCC AACCGCCTCA ACCTGGAGGC CATCAACTAC

ATGGCAGCTG ACGGTGACTT CAAGATCAAA TGTGTGGCCT

TTGACTGA

Gal1 protein sequence (SEQ ID NO: 2):
MACGLVASNL NLKPGECLRV RGEVAPDAKS FVLNLGKDSN

NLCLHFNPRF NAHGDANTIV CNSKDGGAWG TEQREAVFPF

QPGSVAEVCI TFDQANLTVK LPDGYEFKFP NRLNLEAINY

MAADGDFKIK CVAFD
```

The invention is based, in part, on the discovery that Gal1 is overexpressed by RS cells associated with cHLs and that the Gal1 overexpression by RS cells is directly implicated in the development and maintenance of an immunosuppressive Th2/T$_{reg}$-skewed microenvironment in cHL leading to an ineffective host anti-tumor immune response. Gal1 is also shown herein to delineate ALCL. In addition, it is shown herein that Gal1 expression is a highly sensitive and specific marker of pre B-cell acute lymphoblastic leukemia bearing an MLL gene translocation (MLL$^+$ pre B-cell ALL) which is particularly useful for diagnosis.

The Gal1 gene is also expressed in other cells known in the art. See, for example, Rabinovich et al. (2002) *Trends Immunol* 23:313-320; Liu and Rabinovich (2005) *Nature Reviews Cancer* 5:29-41; Rubinstein et al. (2004) *Cancer Cell* 5:241-251; Le et al. (2005) *J Clin Oncol* 23:8932-8941; Vasta et al. (2004) *Curr Opin StructBiol* 14:617-630; Toscano et al. (2007) *Cyt Growth Fact Rev* 18:57-71; Camby et al. (2006) *Glycobiol* 16:137R-157R, each of which is incorporated herein, by reference, in its entirety. Additional studies indicate that Gal1 is also overexpressed in other hematologic malignancies, including certain subtypes of childhood acute lymphoblastic leukemia with adverse prognosis, and can be utilized as a diagnostic and prognostic marker in these diseases (Armstrong et al. (2002) *Nat Genet.* 30:41-47).

II. Gal-1 Antibodies

An isolated Gal1 polypeptide or a fragment thereof (or a nucleic acid encoding such a polypeptide), can be used as an immunogen to generate antibodies that bind to said immunogen, using standard techniques for polyclonal and monoclonal antibody preparation. A full-length Gal1 polypeptide can be used, or alternatively, the invention relates to antigenic peptide fragments of Gal1 polypeptide for use as immunogens. An antigenic peptide of Gal1 comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. Preferred epitopes encompassed by the antigenic peptides are regions of Gal1 that mediate ligand specific carbohydrate binding, e.g., the Gal1 carbohydrate recognition domain, amino acids 30 to 90 of human Gal1, and amino acids 62 to 86 of human Gal1. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an antibody binds substantially specifically to a Gal1 polypeptide, or a fragment thereof. In a preferred embodiment, an antibody binds to a Gal1 polypeptide, or a fragment thereof, and blocks the interaction between a Gal1 polypeptide or a fragment thereof and its natural binding partner(s) or a fragment(s) thereof.

A Gal1 immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating an anti-Gal1 monoclonal antibody (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides antibody can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al (1989) *Science* 246:1275-1281; Griffiths et al. (1993) *EMBO J.* 12:725-734; Hawkins et al. (1992) *J. Mol. Biol.* 226:889-896; Clarkson et al (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-Gal1 polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743.

Additionally, fully human antibodies could be made against a Gal1 immunogen. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified Gal1 immunogen. Spleen cells are harvested and fused to myeloma cells to produce hybridomas. Hybridomas are selected based on their ability to produce antibodies which bind to the Gal1 immunogen. Fully human antibodies would reduce the immunogenicity of such antibodies in a human.

In one embodiment, an antibody for use in the instant invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA*, 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a Gal1 polypeptide or a fragment thereof. In one embodiment, the bispecific antibody could specifically bind to both a Gal1 polypeptide or a fragment thereof and its natural binding partner(s) or a fragment(s) thereof.

Yet another aspect of the invention pertains to anti-Gal1 antibodies that are obtainable by a process comprising, immunizing an animal with an immunogenic Gal1 polypeptide or an immunogenic portion thereof unique to Gal1; and then isolating from the animal antibodies that specifically bind to the polypeptide or a fragment thereof.

In another aspect of this invention, Gal1 polypeptide fragments or variants can be used. In one embodiment, a variegated library of Gal1 variants is generated by combinatorial mutagenesis at the nucleic acid level and is encoded by a variegated gene library. A variegated library of Gal1 variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *NucleicAcid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of Gal1 (Arkin and Youvan (1992) *Proc. Natl. Acad. Sci. USA*

89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes Gal1. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

In one embodiment, the peptide has an amino acid sequence identical or similar to the Gal1 binding site of its natural binding partner(s) or a fragment(s) thereof. In one embodiment, the peptide competes with a Gal1 polypeptide or a fragment thereof for binding its natural binding partner(s) or a fragment(s) thereof. In a preferred embodiment, the peptide carries carbohydrate moieties recognized by a Gal1 polypeptide or a fragment thereof and said peptide competes with the Gal1 polypeptide or a fragment thereof for binding the Gal1 natural binding partner(s) or a fragment(s) thereof.

Peptides can be produced, typically by direct chemical synthesis, and used e.g., as antagonists of the interactions between a Gal1 polypeptide or a fragment thereof and its natural binding partner(s) or a fragment(s) thereof. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, and biochemicalproperties.

Peptidomimetics (Fauchere, J. (1986) *Adv. Drug Res.* 15:29; Veber and Freidinger (1985) *TINS* p. 392; and Evans et al. (1987) *J. Med. Chem.* 30:1229, which are incorporated herein by reference) are usually developed with the aid of computerized molecular modeling. Peptide mimetics that are structurally similar to peptides useful for diagnostic, prognostic, and/or clinical trial monitoring applications can be used to produce equivalent diagnostic, prognostic, and/or clinical trial monitoring applications. Generally, peptidomimetics are structurally similar to a paradigm polypeptide (i.e., a polypeptide that has a biological or pharmacological activity), such as a human Gal1 polypeptide or a fragment thereof, but have one or more peptide linkages optionally replaced by a linkage selected from the group consisting of: —CH2NH—, —CH2S—, —CH2-CH2-, —CH═CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) *CA:* 97:39405 (1982)(—CH(OH)CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds. Derivitization (e.g., labeling) of peptidomimetics should not substantially interfere with the desired diagnostic and/or prognostic utility of the peptidomimetic.

These peptides or peptidomimetic molecules can also be chimeric or fusion proteins. As used herein, a "chimeric protein" or "fusion protein" comprises a protein, peptide, or peptidomimetic molecule or a fragment thereof operatively linked to another protein, peptide, or peptidomimetic molecule or a fragment thereof. A "Gal1 molecule" refers to a polypeptide having an amino acid sequence corresponding to Gal1 or a fragment thereof, whereas a "a non-Gal1 molecule" refers to a polypeptide having an amino acid sequence corresponding to a protein which is not substantially homologous to the respective Gal1 molecule, e.g., a protein which is different from the Gal1 molecule, and which is derived from the same or a different organism. Within a Gal1 fusion protein, the Gal1 portion can correspond to all or a portion of a full length Gal1 molecule. In a preferred embodiment, the fusion protein comprises at least one biologically active portion of a Gal1 molecule, e.g., the carbohydrate recognition domain (CRD). Within the chimeric or fusion protein, the term "operatively linked" is intended to indicate that the independent protein, peptide, or peptidomimetic molecules or fragments thereof are fused in-frame to each other in such a way as to preserve functions exhibited when expressed independently of the fusion.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. Preferably, the first peptide consists of a portion of Gal1 that comprises at least one biologically active portion of a Gal1 molecule, e.g., the carbohydrate recognition domain (CRD). In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). A polypeptide encoding nucleic acid can be cloned into such an expression vector such that the fusion moiety is linked in-frame to the Gal1 encoding sequences.

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between a Gal1 polypeptide or a fragment thereof and its natural binding partner(s) or a fragment(s) thereof.

In yet another aspect of the invention, Gal1 polypeptides or fragments thereof can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other polypeptides which bind to or interact with Gal1 or fragments thereof ("Gal1-binding proteins", "Gal1 binding partners", or "Gal1-bp") and are involved in Gal1 activity. Such Gal1-binding proteins are also likely to be involved in the propagation of signals by the Gal1 polypeptides or Gal1 natural binding partner(s) as, for example, downstream elements of a Gal1-mediated signaling pathway. Alternatively, such Gal1-binding polypeptides may be Gal1 inhibitors.

The two-hybrid system is based on the modular nature of most transcription factors, which consist of separable DNA-binding and activation domains. Briefly, the assay utilizes two different DNA constructs. In one construct, the gene that codes for a Gal1 polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming a Gal1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with the Gal1 polypeptide.

III. Uses and Methods of the Invention

The Gal1 molecules, e.g., the Gal1 nucleic acid molecules, polypeptides, polypeptide homologues, antibodies, and fragments thereof, described herein can be used in one or more of the following methods: a) screening assays; and b) predictive medicine (e.g., diagnostic assays, prognostic assays, and monitoring clinical trials).

The isolated nucleic acid molecules of the invention can be used, for example, to express a Gal1 polypeptide or a fragment thereof and to detect Gal1 mRNA or a fragment thereof (e.g., in a biological sample) or a genetic alteration in a Gal1 gene, as described further below. Moreover, the anti-Gal1 antibodies or fragments thereof of the invention can be used to detect and isolate Gal1 polypeptides or fragments thereof.

A. Screening Assays

In one aspect, the invention relates to a method for preventing in a subject, a disease or condition associated with an unwanted or less than desirable immune response. Subjects at risk for a disease that would benefit from treatment with the claimed agents or methods can be identified, for example, by any or a combination of diagnostic or prognostic assays known in the art and described herein (see, for example, agents and assays described in III. Methods of Selecting Agents that Modulate Immune Cell Activation).

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the Gal1 nucleotide sequences, described herein, can be used to map the location of the Gal1 genes on a chromosome. The mapping of the Gal1 sequences to chromosomes is an important first step in correlating these sequences with genes associated with disease.

Briefly, Gal1 genes can be mapped to chromosomes by preparing PCR primers (preferably 15-25 bp in length) from the Gal1 nucleotide sequences. Computer analysis of the Gal1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the Gal1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio, P. et al. (1983) *Science* 220: 919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the Gal1 nucleotide sequences to design oligonucleotide primers, sublocalization can be achieved with panels of fragments from specific chromosomes. Other mapping strategies which can similarly be used to map a Gal1 sequence to its chromosome include in situ hybridization (described in Fan, Y. et al. (1990) Proc. Natl. Acad. Sci. USA 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data (such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature 325:783-787.

Moreover, differences in the DNA sequences between individuals affected and unaffected with a disease associated with the Gal1 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The Gal1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the Gal1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The Gal1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of Gal1 can provide positive individual identification with a panel of perhaps 10 to 1,000 primers which each yield a noncoding amplified sequence of 100 bases. If predicted Gal1 coding sequences are used, a more appropriate number of primers for positive individual identification would be 500-2000.

If a panel of reagents from Gal1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Gal1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of Gal1 are particularly appropriate for this use as greater numbers of polymorphisms occur in the noncoding regions, making it easier to differentiate individuals using this technique. Examples of polynucleotide reagents include the Gal1 nucleotide sequences or portions thereof, e.g., fragments derived from the noncoding regions of Gal1 having a length of at least 20 bases, preferably at least 30 bases.

The Gal1 nucleotide sequences described herein can further be used to provide polynucleotide reagents, e.g., labeled or labelable probes which can be used in, for example, an in situ hybridization technique, to identify a specific tissue, e.g., lymphocytes. This can be very useful in cases where a forensic pathologist is presented with a tissue of unknown origin. Panels of such Gal1 probes can be used to identify tissue by species and/or by organ type.

In a similar fashion, these reagents, e.g., Gal1 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining Gal1 polypeptide and/or nucleic acid expression as well as Gal1 activity, in the context of a biological sample (e.g., blood, serum, cells, or tissue) to thereby determine whether an individual is afflicted with a disease or disorder, or is at risk of developing a disorder, associated with aberrant or unwanted Gal1 expression or activity. The invention also provides for prognostic (or predictive) assays for determining whether an individual is at risk of developing a disorder associated with Gal1 polypeptide, nucleic acid expression or activity. For example, mutations in a Gal1 gene can be assayed in a biological sample.

Such assays can be used for prognostic or predictive purpose to thereby prophylactically treat an individual prior to the onset of a disorder characterized by or associated with Gal1 polypeptide, nucleic acid expression or activity.

Another aspect of the invention pertains to monitoring the influence of agents (e.g., drugs, compounds) on the expression or activity of Gal1 in clinical trials. These and other agents are described in further detail in the following sections.

1. Diagnostic Assays

An exemplary method for detecting the presence or absence of Gal1 polypeptide or nucleic acid or fragments thereof in a biological sample involves obtaining a biological sample from a test subject and contacting the biological sample with a compound or an agent capable of detecting Gal1 polypeptide or nucleic acid that encodes Gal1 polypeptide (e.g., mRNA or genomic DNA) or fragments thereof such that the presence of Gal1 polypeptide or nucleic acid or fragments thereof is detected in the biological sample. A preferred agent for detecting Gal1 mRNA, genomic DNA, or fragments thereof is a labeled nucleic acid probe capable of hybridizing to Gal1 mRNA, genomic DNA, or fragments thereof. The nucleic acid probe can be, for example, full length Gal1 nucleic acid, or a portion thereof, such as an oligonucleotide of at least 15, 30, 50, 100, 250 or 500 nucleotides in length and sufficient to specifically hybridize under stringent conditions to Gal1 mRNA or genomic DNA. Other suitable probes for use in the diagnostic assays of the invention are described herein.

A preferred agent for detecting a Gal1 polypeptide or a fragment thereof is an antibody capable of binding to a Gal1 polypeptide, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect Gal1 mRNA, polypeptide, genomic DNA, or fragments thereof, in a biological sample in vitro as well as in vivo. For example, in vitro techniques for detection of Gal1 mRNA or a fragment thereof include Northern hybridizations and in situ hybridizations. In vitro techniques for detection of Gal1 polypeptide include enzyme linked immunosorbent assays (ELISAs), Western blots, immunoprecipitations and immunofluorescence. In vitro techniques for detection of Gal1 genomic DNA or a fragment thereof include Southern hybridizations. Furthermore, in vivo techniques for detection of a Gal1 polypeptide or a fragment thereof include introducing into a subject a labeled anti-Gal1 antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Gal1 polypeptide, mRNA, genomic DNA, or fragments thereof, such that the presence of Gal1 polypeptide, mRNA, genomic DNA, or fragments thereof, is detected in the biological sample, and comparing the presence of Gal1 polypeptide, mRNA, genomic DNA, or fragments thereof, in the control sample with the presence of Gal1 polypeptide, mRNA, genomic DNA, or fragments thereof in the test sample.

The invention also encompasses kits for detecting the presence of a Gal1 nucleic acid, polypeptide, or fragments thereof, in a biological sample. For example, the kit can comprise a labeled compound or agent capable of detecting a Gal1 nucleic acid, polypeptide, or fragments thereof in a biological sample; means for determining the amount of the Gal1 nucleic acid, polypeptide, or fragments thereof in the sample; and means for comparing the amount of the Gal1 nucleic acid, polypeptide, or fragments thereof in the sample with a standard. The compound or agent can be packaged in a suitable container. The kit can further comprise instructions for using the kit to detect the Gal1 nucleic acid, polypeptide, or fragments thereof.

2. Prognostic Assays

The diagnostic methods described herein can furthermore be utilized to identify subjects having or at risk of developing a disease or disorder associated with aberrant or unwanted Gal1 expression or activity. As used herein, the term "aberrant" includes a Gal1 expression or activity which deviates from the wild type Gal1 expression or activity. Aberrant expression or activity includes increased or decreased expression or activity, as well as expression or activity which does not follow the wild type developmental pattern of expression or the subcellular pattern of expression. For example, aberrant Gal1 expression or activity is intended to include the cases in which a mutation in the Gal1 gene or regulatory sequence thereof causes the Gal1 gene to be under-expressed or over-expressed and situations in which such mutations result in a non-functional Gal1 polypeptide or a polypeptide which does not function in a wild-type fashion, e.g., a polypeptide which does not interact with a Gal1 binding partner(s) or one which interacts with a non-Gal1 binding partner(s). As used herein, the term "unwanted" includes an unwanted phenomenon involved in a biological response such as immune cell activation. For example, the term unwanted includes a Gal1 expression or activity which is undesirable in a subject.

The assays described herein, such as the preceding diagnostic assays or the following assays, can be utilized to identify a subject having or at risk of developing a disorder associated with a misregulation in Gal1 polypeptide activity or nucleic acid expression, such as an autoimmune disorder, an immunodeficiency disorder, an immune system cancer, e.g., Hodgkin lymphoma, anaplastic large cell lymphoma, or MLL$^+$ pre B-cell ALL. Alternatively, the prognostic assays can be utilized to identify a subject having or at risk for developing a disorder associated with a misregulation of Gal1 polypeptide activity or nucleic acid expression, such as an autoimmune disorder, and immunodeficiency disorder, or an immune system cancer, e.g., Hodgkin lymphoma, anaplastic large cell lymphoma, or MLL$^+$ pre B-cell ALL. Thus, the present invention provides a method for identifying a disease or disorder associated with aberrant or unwanted Gal1 expression or activity in which a test sample is obtained from a subject and Gal1 polypeptide or nucleic acid (e.g., mRNA or genomic DNA) is detected, wherein the presence of Gal1 polypeptide or nucleic acid is diagnostic for a subject having or at risk of developing a disease or disorder associated with aberrant or unwanted Gal1 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant or unwanted Gal1 expression or activity. For example, such methods can be used to determine whether a subject can be effectively treated with an agent for an autoimmune disorder, immunodeficiency disorder, or immune system cancer, e.g., Hodgkin lymphoma, anaplastic large cell lymphoma, or MLL$^+$ pre B-cell ALL. Thus, the present invention provides methods for determining whether a subject can be effectively treated with an agent for a disorder associated with aberrant or unwanted Gal1 expression or activity in which a test sample is obtained and Gal1 polypeptide or nucleic acid expression or activity is detected (e.g., wherein the abundance of Gal1 polypeptide or nucleic acid expression or activity is diagnostic for a subject that can be administered the agent to treat a disorder associated with aberrant or unwanted Gal1 expression or activity).

The methods of the invention can also be used to detect genetic alterations in a Gal1 gene, thereby determining if a subject with the altered gene is at risk for a disorder characterized by misregulation in Gal1 polypeptide activity or nucleic acid expression, such as an autoimmune disorder, an immunodeficiency disorder, or an immune system cancer, e.g., Hodgkin lymphoma, anaplastic large cell lymphoma, or MLL$^+$ pre B-cell ALL. In preferred embodiments, the methods include detecting, in a sample of cells from the subject, the presence or absence of a genetic alteration characterized by at least one alteration affecting the integrity of a gene encoding a Gal1 polypeptide, or the mis-expression of the Gal1 gene. For example, such genetic alterations can be detected by ascertaining the existence of at least one of 1) a deletion of one or more nucleotides from a Gal1 gene, 2) an addition of one or more nucleotides to a Gal1 gene, 3) a substitution of one or more nucleotides of a Gal1 gene, 4) a chromosomal rearrangement of a Gal1 gene, 5) an alteration in the level of a messenger RNA transcript of a Gal1 gene, 6) aberrant modification of a Gal1 gene, such as of the methylation pattern of the genomic DNA, 7) the presence of a non-wild type splicing pattern of a messenger RNA transcript of a Gal1 gene, 8) a non-wild type level of a Gal1 polypeptide, 9) allelic loss of a Gal1 gene, and 10) inappropriate post-translational modification of a Gal1 polypeptide. As described herein, there are a large number of assays known in the art which can be used for detecting alterations in a Gal1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a Gal1 gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a Gal1 gene under conditions such that hybridization and amplification of the Gal1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Gal1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Gal1 can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in Gal1 can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Gal1 gene and detect mutations by comparing the sequence of the sample Gal1 with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad. Sci. USA 74:5463. It is also contemplated that any of a variety of automated sequencing procedures can be utilized when performing the diagnostic assays (Naeve, C. W. (1995) *Biotechniques* 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the Gal1 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type Gal1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Gal1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a Gal1 sequence, e.g., a wild-type Gal1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Gal1 genes. For example, single strand conformation polymorphism (SSCP) may be used to detect differences in electrophoretic mobility between mutant and wild type nucleic acids (Orita et al. (1989) Proc Natl. Acad. Sci. USA 86:2766; see also Cotton (1993) Mutat. Res. 285:125-144 and Hayashi (1992) Genet. Anal. Tech. Appl. 9:73-79). Single-stranded DNA fragments of sample and control Gal1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell. Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Gal1 gene.

Furthermore, any cell type or tissue in which Gal1 is expressed may be utilized in the prognostic assays described herein.

3. Monitoring of Effects During Clinical Trials

Monitoring the influence of agents (e.g., drugs) on the expression or activity of a Gal1 polypeptide or a fragment thereof (e.g., the modulation of cell proliferation and/or migration) can be applied not only in basic drug screening, but also in clinical trials. For example, the effectiveness of an agent determined by a screening assay as described herein to increase Gal1 gene expression, polypeptide levels, or upregulate Gal1 activity, can be monitored in clinical trials of subjects exhibiting decreased Gal1 gene expression, polypeptide levels, or downregulated Gal1 activity. Alternatively, the effectiveness of an agent determined by a screening assay to decrease Gal1 gene expression, polypeptide levels, or downregulate Gal1 activity, can be monitored in clinical trials of subjects exhibiting increased Gal1 gene expression, polypeptide levels, or Gal1 activity. In such clinical trials, the expression or activity of a Gal1 gene, and preferably, other genes that have been implicated in, for example, a Gal1-associated disorder can be used as a "read out" or marker of the phenotype of a particular cell.

For example, and not by way of limitation, genes, including Gal1, that are modulated in cells by treatment with an agent (e.g., compound, drug or small molecule) which modulates Gal1 activity (e.g., identified in a screening assay as described herein) can be identified. Thus, to study the effect of agents on Gal1-associated disorders (e.g., disorders characterized by dysregulated Gal1 activity), for example, in a clinical trial, cells can be isolated and RNA prepared and analyzed for the levels of expression of Gal1 and other genes implicated in the Gal1-associated disorder, respectively. The levels of gene expression (e.g., a gene expression pattern) can be quantified by Northern blot analysis or RT-PCR, as described herein, or alternatively by measuring the amount of polypeptide produced, by one of the methods as described herein, or by measuring the levels of activity of Gal1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression of a Gal1 polypeptide, mRNA, genomic DNA, or fragments thereof in the preadministration sample; (iii) obtaining one or more post-administration samples from the subject; (iv) detecting the level of expression or activity of the Gal1 polypeptide, mRNA, genomic DNA, or fragments thereof in the post-administration samples; (v) comparing the level of expression or activity of the Gal1 polypeptide, mRNA, genomic DNA, or fragments thereof in the pre-administration sample with the Gal1 polypeptide, mRNA, or genomic DNA in the post administration sample or samples; and (vi) altering the administration of the agent to the subject accordingly. For example, increased administration of the agent may be desirable to increase the expression or activity of Gal1 to higher levels than detected, i.e., to increase the effectiveness of the agent. Alternatively, decreased administration of the agent may be desirable to decrease expression or activity of Gal1 to lower levels than detected, i.e., to decrease the effectiveness of the agent. According to such an embodiment, Gal1 expression or activity may be used as an indicator of the effectiveness of an agent, even in the absence of an observable phenotypic response.

This invention is further illustrated by the following examples which should not be construed as limiting. The contents of all references, patents and published patent applications cited throughout this application, as well as the Figures, are incorporated herein by reference.

EXAMPLES

Example 1: Materials and Methods Used in Examples 2-3

A. Cell Lines

Twenty-one DLBCL cell lines (Ly19, Ly18, Ly10, Ly8, Ly7, Ly4, Ly3, Ly1, Pleiffer, DHL10, DHL8, DHL7, DHL6, DHL5, DHL4, DB, HT WSU, Karpas 422, Toledo and Farage), 1 MLBCL cell line (Karpas 1106) and 7 cHL cell lines (KMH2, HDLM2, SupHD1, L1236, L540, L428, HD-MY-Z) were maintained as previously described (Mathas et al. (2002) *Embo J* 21, 4104-4113; Smith et al. (2005) *Blood* 105, 308-316). The cHL cell lines were previously demonstrated to have constitutive AP-1 activity and increased expression of c-JUN and JUNB (Mathas et al. (2002) *Embo J* 21, 4104-4113).

B. Identification of Genes Overexpressed in cHL Cell Lines by Gene Expression Profiling Total RNAs from a panel of 21 diffuse large B-cell lymphoma (DLBCL) and 7 cHL cell lines were hybridized to U133A and B Affymetrix oligonucleotide microarrays, and the chips were scanned and data analyzed as previously described (Monti et al. (2005) *Blood* 105, 1851-1861). The top 9,586 genes that met threshold and variation index criteria were analyzed with GenePattern program (available at the M.I.T. Broad Institute's website) to identify differentially expressed genes in cHL and DLBCL. Genes correlated with the class template (HL vs. DLBCL) were identified by ranking them according to their signal-to-noise ratio (SNR). For each gene, a specific p-value based on permutation testing was calculated and corrected for false discovery rate by the Benjamini and Hochberg procedure (Benjamini et al. (2001) *Behav Brain Res* 125, 279-284; Reiner et al. (2003) *Bioinformatics* 19, 368-375).

C. Analysis of Gal1 Expression in Cell Lines by Immunoblot

DLBCL and cHL cell lines were maintained as previously described (Mathas et al. (2002) *Embo J* 21, 4104-4113; Polo et al. (2007) *Proc Natl Acad Sci USA* 104, 3207-3212). Cells were lysed, size-fractionated on NuPAGE® Novex® 4-12% Bis-Tris Gels (Invitrogen, Carlsbad, Calif.), and transferred to PVDF membranes (Millipore Corp., Bedford, Mass.). Membranes were immunostained with purified Gal1 rabbit IgG (Rubinstein et al. (2004) *Cancer Cell* 5, 241-251) and HRP-conjugated donkey anti-rabbit antibody (GE Healthcare, Piscataway, N.J.) and developed using a chemiluminescent method (ECL™, GE Healthcare).

D. Immunohistochemistry

Immunohistochemistry was performed as previously described (Juszczynski et al. (2006) *Mol Cell Biol* 26, 5348-5359) using 5 µm thick formalin-fixed, paraffin-embedded tissue sections of newly diagnosed primary cHLs and DLBCLs and purified Gal1 rabbit IgG.

E. Analysis of Regulatory Elements in the Gal1 Locus and Generation of Gal1 Enhancer Constructs Computational analysis of the Gal1 locus (chr22:36,400,510-36,406,802, alignment with Human NCBI Genome assembly v36, March 2006) was performed with the publicly available version of Genomatix suite (available at the Genomatix company website) (Scherf et al. (2000) *J Mol Biol* 297, 599-606) and rVISTA (available at the dcode.org website) (Loots and Ovcharenko (2004) *Nucleic Acids Res* 32, W217-221) and a putative downstream regulatory element (enhancer) containing a conserved AP1 binding site was identified (+1567 to +1675). To generate a series of Gal1 promoter-enhancer reporter constructs, the Gal1 promoter region (−403+67) was amplified using PCR and this sequence was ligated into the pGL3 promoterless reporter vector (Promega, Madison, Wis.), generating pGL3-Gal1-403+67-Luc. Thereafter, fragments spanning nucleotides +459+1746, +459+777, and +1346+1746 from the Gal1 transcription start site (TSS) were PCR-amplified and cloned into pGL3-Gal1-403+67-Luc 3' of the luciferase gene. Deletions in AP1 site (TGACTCA to TGxxxCA) were generated using the pGL3-Gal1-403+67-Luc-e1346+1746 construct and the GeneTailor™ Site-Directed Mutagenesis System (Invitrogen) as recommended by the manufacturer. An additional set of constructs was generated with the candidate enhancer elements cloned upstream of the Gal1 promoter.

F. Generation of Dominant Negative cJun Constructs

Dominant-negative cJun constructs were generated as previously described (Ludes-Meyers et al. (2001) *Oncogene* 20, 2771-2780) with minor modifications. A cJun fragment which lacked the transactivation domain (amino acids 123 to 223) was PCR-amplified from intronless cJUN genomic DNA and ligated in the pFLAG-CMV2 vector (pFLAG-CMV2-cJUNDN) (Sigma Aldrich, St Louis, Mo.) using forward primer, CAAGAATTCCCAGAACACGCTGC-CCAGCGTC (SEQ ID NO: 3), and reverse primer, GAATCTAGAGTCGCAACTTGTCAAGTTCT-CAAGTCTGTC (SEQ ID NO: 4).

G. Analysis of Gal1 Promoter—Enhancer Constructs with Luciferase Assays

The HD-MY-Z cHL and SU-DHL7 DLBCL cell lines were grown to 60-80% confluency on 24 well-plates and cotransfected with 300 ng/well of the appropriate promoter-enhancer pGL3 construct (wild-type or mutant Gal1) and 100 ng/well of the control reporter plasmid, pRL-TK (Promega) using FuGENE® 6 transfection reagent (Roche Applied Science) according to the manufacturer's protocol. For cotransfection experiments with cJUN-DN-FLAG, HD-MY-Z cells were transfected with 150 ng of pGL3-Gal1-403+67-Luc-e1346+1746, 250 ng of pFLAG-CMV2-cJUN-DN and 100 ng of pRL-TK. After 24 hours of incubation, cells were lysed and luciferase activities were determined by a chemiluminescence assay using the Dual Luciferase® Assay kit (Promega) and Luminoskan Ascent® luminometer (Thermo Lab Systems, Franklin, Mass.) as described (Juszczynski et al. (2006) *Mol Cell Biol* 26, 5348-5359).

H. Electrophoretic Mobility Shift Analyses of the AP1-Binding Site in the Gal1 Enhancer Nuclear extracts from three cHL cell lines (HD-MY-Z, L428 and SupHD-1) and 3 DLBCL cell lines (SU-DHL7, SU-DHL4 and Toledo) were obtained as previously described (Juszczynski et al. (2006) *Mol Cell Biol* 26, 5348-5359). Double-stranded wild-type (WT) and mutant probes corresponding to AP1-binding region in Gal1 enhancer (wild-type, WT [5'-TTTTCTGGG TGACTCACTTCCCCCG-3' (SEQ ID NO: 5)] and mutant, MUT [5'-TTTTCTGGGTtcagtACTTCCCCCG-3' (SEQ ID NO: 6) [mutant bases in lower case]) were end-labelled with [γ-$^{32}$P]ATP, purified and used in binding reactions as described (Juszczynski et al. (2006) *Mol Cell Biol* 26, 5348-5359). DNA binding was carried out using 5 μg of nuclear extracts and approximately 10,000 cpm of radiolabelled probe in 20 μL of binding buffer (Juszczynski et al. (2006) *Mol Cell Biol* 26, 5348-5359). After 30 minutes of incubation, reactions were loaded on a 5% polyacrylamide gel and electrophoresed. Gels were vacuum dried and exposed to x-ray films overnight at −80° C. For competitor studies, 100× molar excess of unlabelled wild-type or mutant probe was included in the binding reactions. For supershift studies, 1 μL of c-JUN antibody or (3-actin (Santa Cruz Biotechnology, Santa Cruz, Calif. and Sigma-Aldrich, respectively) was added to the reaction 15 min prior to the probe.

I. Q-PCR Analysis of Gal1 Transcript Abundance Following AP1 Inhibition

The HD-MY-Z cHL cell line was grown to 60-80% confluency on 100 mm plates and transiently transfected with 15 μg of pFLAG-CMV2 (empty vector) or pFLAGCMV2-cJUNDN plasmids using FuGENE® 6 transfection reagent (Roche Applied Science) according to the manufacturer's protocol. After 72 hours of culture, RNA was extracted using Trizol® reagent (Invitrogen) and cDNA was synthesized from total RNA (3 μg) using SuperScript® II reverse transcriptase (Invitrogen) and random hexamer primers. Gal1 and GAPDH (housekeeping control) transcript abundance was evaluated by QPCR using Power SYBR® green PCR Master Mix (Applied Biosystems, Foster City, Calif.) and the following primers: GAPDH, Forward: GATTCCACCCATGGCAAATTC; GAPDH, Reverse: TGATTTTGG AGGGATCTCGCTC; Gal1, Forward: TCGCCAGCAACCTGAATCTC, Gal1, Reverse: GCACGAAGCTCTTAGCGTCA. PCR was performed using an ABI PRISM® 7700 thermal cycler (Applied Biosystems) and threshold Cycle ($C_T$) values were generated using the Sequence Detection Software, version 1.2 (Applied Biosystems). Gal1 transcript abundance was calculated relative to the housekeeping control GAPDH using the $2^{-(\Delta CTGal1-\Delta CTGAPDH)}$ method according to the manufacturer's instructions. Standard deviations were calculated from triplicate ΔΔCT values.

J. Statistical Analysis

All statistical analyses were done using Statistica 6.0 software (Statistica, Tulsa, Okla.). Students t test was used for comparisons between 2 groups; Anova was used for multiple comparisons.

Example 2: Overexpression of Gal1 in cHL RS Cells

To identify novel cHL-specific T-cell inhibitory molecules, the gene expression profiles of a series of cHL and diffuse large B-cell lymphoma (DLBCL) and mediastinal LBCL (MLBCL) cell lines were compared. Gal1 transcripts were 4- to 29-fold more abundant in cHL cell lines than in the LBCL lines (p=0.002, FDR=0.014, FIGS. 1A and 1B). Gal1 protein expression was also uniformly high in cHL cell lines and low or undetectable in DLBCL and MLBCL lines by western blotting (FIG. 1C). Immunohistochemical staining of primary tumor sections revealed abundant Gal1 expression in cHL RS cells, whereas LBCLs were uniformly negative (FIG. 1D). In a series of primary lymphoid tumors, 10/10 cHLs were Gal1+ whereas 10/10 primary DLBCLs and 5/5 primary mediastinal LBCLs (MLBCLs) lacked Gal1 expression. Taken together, these data indicate that Gal1 is selectively upregulated in the RS cells of cHLs.

Example 3: RS Cell Gal1 Expression is Regulated by an AP1-Dependent Enhancer

Figure 2:
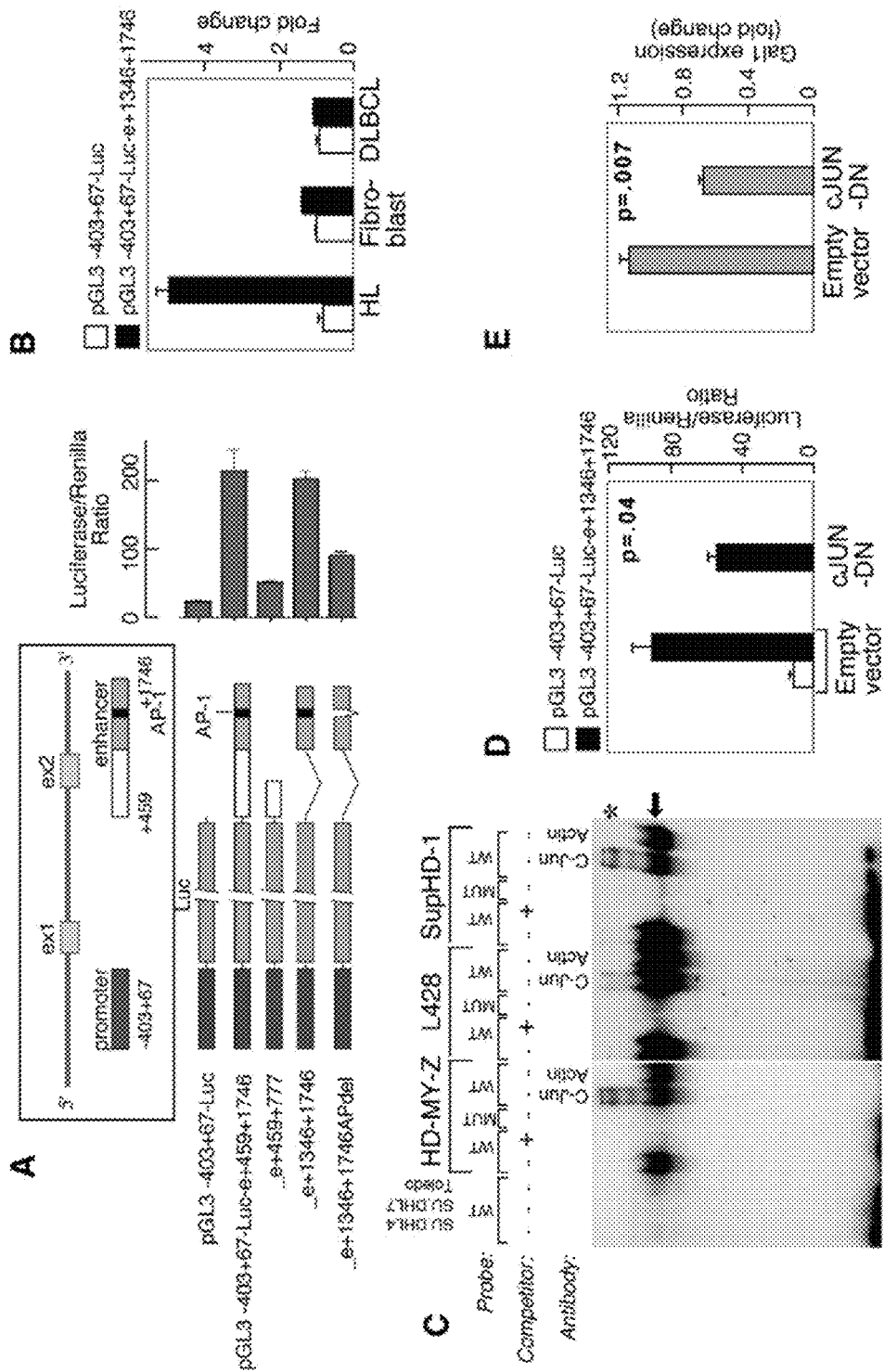
FIGS. 2A-2E shows that Gal1 transcription is regulated by an AP1-dependent enhancer.

To elucidate the mechanisms responsible for Gal1 overexpression in cHL RS cells, the Gal1 locus on chromosome 22 was analyzed. A candidate GC-rich regulatory element with a conserved putative AP1 binding site approximately 1.5 kb downstream of the Gal1 transcription start site (TSS) was identified. Since the AP1 components, cJUN and JUN-B are overexpressed in cHL and are critical for the pathogenesis of the disease (Mathas et al. (2002) *EMBO J.* 21: 4104-4113), it was asked whether AP1 mediates Gal1 expression in cHL. Luciferase vectors driven by the previously described Gal1 promoter (−403+67) were generated (Salvatore et al. (1998) *FEBS Lett* 421:152-8) and the putative Gal1 enhancer element (or mutated controls) and assessed associated luciferase activity in a cHL cell line (HD-MY-Z) known to have constitutive activation of AP1 (FIG. 2A) (Mathas et al. (2002) *EMBO J.* 21: 4104-4113). Constructs including the GC-rich regulatory element (bp+459+1746 or +1346+1746) upregulated luciferase expression ~8-10 fold, whereas constructs lacking the candidate sequence (+459+777) or containing a deletion in the AP1-binding site (+1346+1746$_{del}$) exhibited significantly lower luciferase activity (FIG. 2A). Similar results were obtained with a set of constructs in which the regulatory element was cloned upstream of the Gal1 promoter, demonstrating that the identified sequence (bp+1346+1746) is a bona fide Gal1 enhancer.

Given the AP1 dependence of the Gal1 enhancer and the constitutive AP1 activity in cHL (Mathas et al. (2002) *EMBO J.* 21: 4104-4113), it was next asked whether the Gal1 enhancer was selectively active in this disease. For these experiments, cHL, DLBCL and fibroblast cell lines were transfected with either the Gal1 promoter-only vector (pGL3-Gal1$_{-403+67}$-Luc) or the promoter-enhancer construct (pGL3-Gal1$_{403+67}$-Luc-e$_{1346-1746}$) and compared the respective luciferase activities (FIG. 2B). The Gal1 promoter-enhancer construct specifically upregulated luciferase expression in cHL cells but not DLBCL cells or fibroblasts (FIG. 2B).

After demonstrating the specificity and activity of the Gal1 AP1 enhancer element in a cHL cell line (FIGS. 2A and 2B), the requirement for AP1 transcription factors in electrophoretic mobility shift assays was directly evaluated (FIG. 2C). Nuclear extracts from 3 cHL and 3 DLBCL cell lines were incubated with radiolabelled wild-type or mutant probes corresponding to an AP1 element in the Gal1 enhancer. Gal1 wild type, but not mutant probe, directly bound to nuclear proteins extracted from cHL, but not DLBCL, cell lines (FIG. 2C). The complexes formed with Gal1 WT probe were displaced by unlabeled WT competitor, further confirming the binding specificity (FIG. 2C). In supershift assays, the Gal1/AP1 complex was retarded by cJun antibody (FIG. 2C). Furthermore, the simultaneous overexpression of a dominant negative cJUN construct (cJUN-DN) reduced Gal1-driven luciferase activity in cHL cells (FIG. 2D). In addition, when AP1 was at least partially inhibited via the overexpression of cJUN-DN, there was a significant decrease in Gal1 transcript abundance in cHL cells (FIG. 2E). Taken together, these studies indicate that cHL RS cells selectively overexpress Gal1, at least in part, via an AP1-driven enhancer.

Examples 1-3 describe the overexpression of Gal1 by cHL RS cells. Although cHL RS cells exhibit near uniform Gal1 expression, DLBCLs and MLBCL are largely Gal1 negative, prompting speculation that Gal1 may distinguish cHL from certain "grey zone" lymphomas that share characteristics of DLBCL and cHL (Abramson and Shipp (2005) Blood 106, 1164-1174). A common feature of these "grey zone" lymphomas is an increased host inflammatory response, highlighting the interaction between the tumor cells and their host microenvironment (Abramson and Shipp (2005) Blood 106, 1164-1174). Gal1 overexpression is a defining feature of cHL that is not shared with its closely related counterpart, primary MLBCL (Savage et al. (2003) Blood 102, 3871-3879), providing insights into the relative efficacy of host immune responses in these tumors.

Figure 3:
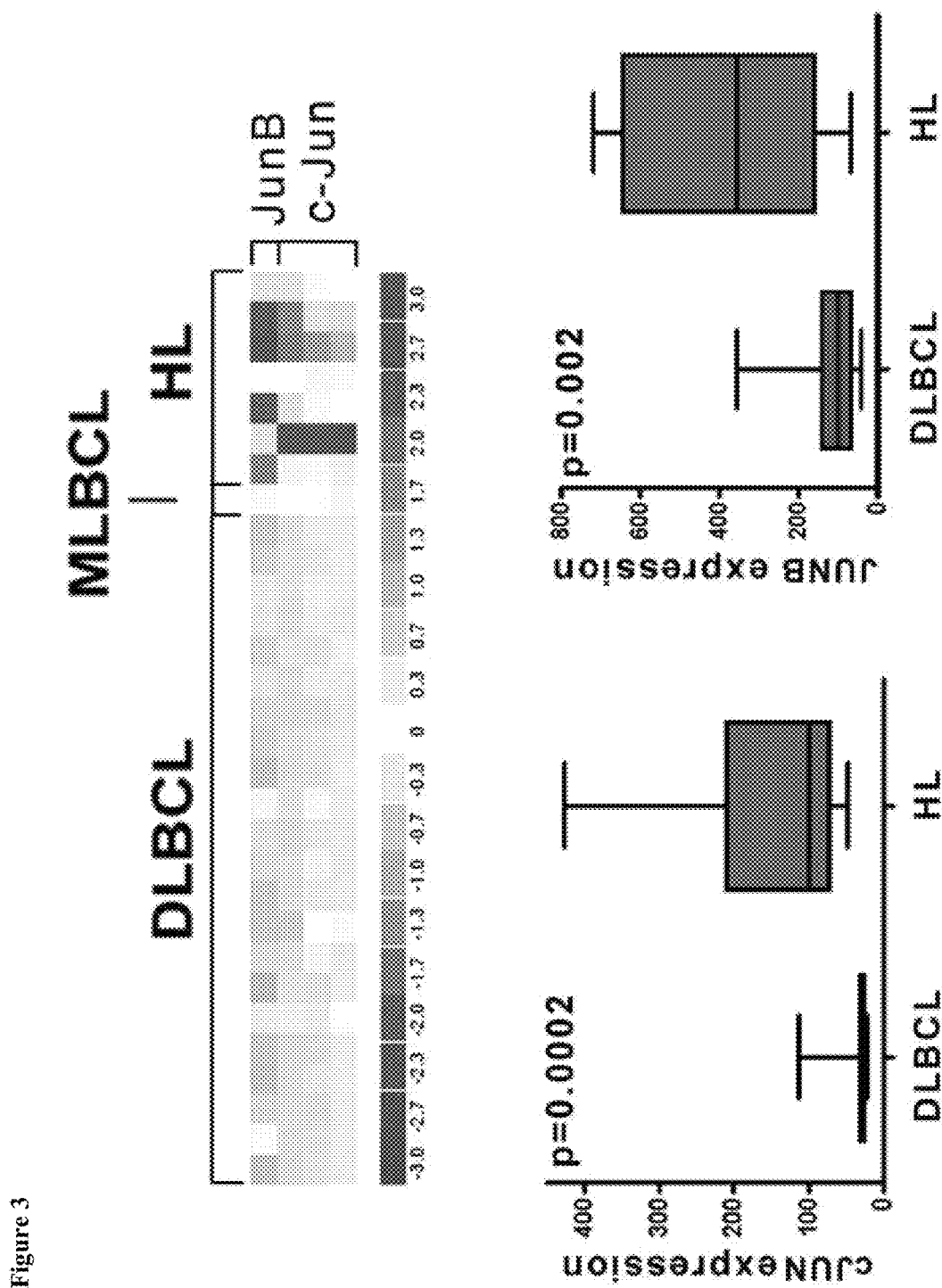
FIG. 3 shows cJUN and JUN-B expression in LBCL and cHL cell lines. The relative abundance of cJUN and JUN-B transcripts in DLBCL, MLBCL and cHL cell lines is shown. The color scale at the bottom indicates the relative expression and standard deviations from the mean. The plots represent the median expression of Gal1 (horizontal line) in LBCL versus cHL cell lines ±25-75 percentile (bars) and ± range (whiskers). Statistical differences in the relative cJUN and JUN-B expression in DLBCL and cHL cell lines were evaluated using a Mann-Whitney U test.

The differential expression of Gal1 in these lymphomas is likely due to the cHL-specific overexpression of the AP1 transcription factor components, cJUN and JUNB, and the constitutive activation of the AP1 pathway (Mathas et al. (2002) Embo J 21, 4104-4113; FIG. 3). Gal1 expression is regulated, at least in part, by a cHL-specific, AP1-driven enhancer. AP1 also functions in synergy with NF-κB to control the proliferation and limit the apoptosis of cHL RS cells (Mathas et al. (2002) Embo J 21, 4104-4113). Therefore, in addition to its pro-survival functions in cHL RS cells, AP1 also regulates the interplay between RS cells and the tumor microenvironment through a Gal1-mediated pathway.

Example 4: Materials and Methods Used in Examples 5-8

A. Case Selection

Cases were derived from the files of Brigham & Women's Hospital (BWH). All diagnoses were established at the time of the original biopsy evaluation and based on the criteria established by the current WHO classification system (Jaffe et al. (2001) Pathology and Genetics of Tumours of Hematopoietic and Lymphoid Tissues, Lyon, IARC Press). Diagnoses were subsequently confirmed during re-review as part of this study.

B. Immunohistochemistry

Immunohistochemistry was performed using 5μ thick formalin- or B5-fixed, paraffin-embedded tissue sections on individual slides as previously described (Rodig et al. (2005) Am. J. Surg. Pathol. 29, 196-203). Briefly, slides were soaked in xylene, passed through graded alcohols, and then pre-treated with 10-mM citrate, pH 6.0 (Zymed, South San Francisco, Calif.) in a steam pressure cooker (Decloaking Chamber™, BioCare Medical, Walnut Creek, Calif.) as per manufacturer's instructions. All further steps were performed at room temperature in a hydrated chamber. Slides were then treated with Peroxidase Block (DAKO USA, Carpinteria, Calif.) for 5 minutes to quench endogenous peroxidase activity. One of two primary rabbit polyclonal anti-Gal1 antibodies (1:10,000 dilution; generated in the laboratory of G.A.R.) (Rubinstein et al. (2004) Cancer Cell 5:241-251; Juszczynski et al. (2007) Proc. Natl. Acad. Sci. USA 104:13134-13139) primary rabbit monoclonal anti-c-Jun (1:50 dilution, clone 60A8, cat. #9165, Cell Signaling Technology, Danvers, Mass.), or primary monoclonal rabbit anti-phospho-c-Jun specific for phosphorylated serine at amino acid position 63 (1:50 dilution, clone 54B3, cat. #2361, Cell Signaling Technology) was applied in DAKO diluent (DAKO) for 1 hour at room temperature. Slides were washed in 50-mM Tris-Cl, pH 7.4, and anti-rabbit or anti-murine horseradish peroxidase-conjugated antibody solution (Envision+detection kit, DAKO) was applied for 30 minutes. After further washing, immunoperoxidase staining was developed using a diaminobenzidine (DAB) chromogen kit (DAKO) per the manufacturer and counterstained with Harris hematoxylin (Polyscientific, Bay Shore, N.Y.).

C. Immunohistochemical Evaluation

Reactivity for Galectin-1, c-Jun, and phospho-c-Jun for all cases was determined and scored independently by two hematopathologists (SJR and JLK). Intensity of staining for Galectin-1 was scored as follows: (0)=no staining detected, (1+)=weak staining, (2+)=moderate staining, (3+)=strong staining of the tumor cells. Positive staining for a case was defined as 2+ or 3+cytoplasmic staining in >50% of the tumor cells. 0 or 1+ staining in >50% of tumor cells, or focal reactivity at an intensity of 2+ or 3+ in <50% of the tumor cells was considered negative. Positive staining of endothelial cells and macrophages served as positive internal controls. Staining for c-Jun and phospho-c-Jun was considered positive if nuclear staining for the antigen was observed >50% and >25% of the interphase tumor nuclei, respectively. Staining of endothelial and dendritic cells served as internal positive controls for both antibodies. All cases were photographed at 1000× original magnification with an Olympus BX41® microscope with the objective lens of 100×/0.75 Olympus UPlanFL® (Olympus, Melville, N.Y.). The pictures were taken using Olympus QColor3™ and analyzed with acquisition software QCapture™ v. 260 (QImaging, Burnaby, BC, Canada) and Adobe® Photoshop® 6.0 (Adobe, San Jose, Calif.).

Example 5: Expression of Gal1 by Cancer Cells

To determine whether Gal1 expression is a diagnostically useful distinguishing feature of primary cHL, an extensive series of cHLs (72 cases) was examined by immunohistochemistry. These primary tumors included the 2 major subtypes of cHL: nodular sclerosis (NSHL, 45 cases) and mixed cellularity (MCHL, 15 cases). In addition, the cohort included several cases diagnosed as cHL not otherwise specified (cHL nos, 11 cases) and the rare lymphocyte-rich subtype (LRHL, 1 case). A subset of cases was also evaluated for evidence of Epstein-Barr virus (EBV) infection by in situ hybridization for Epstein Barr virus encoded RNAs (EBER) (EBER+, 10 cases; EBER−, 33 cases).

Figure 4:
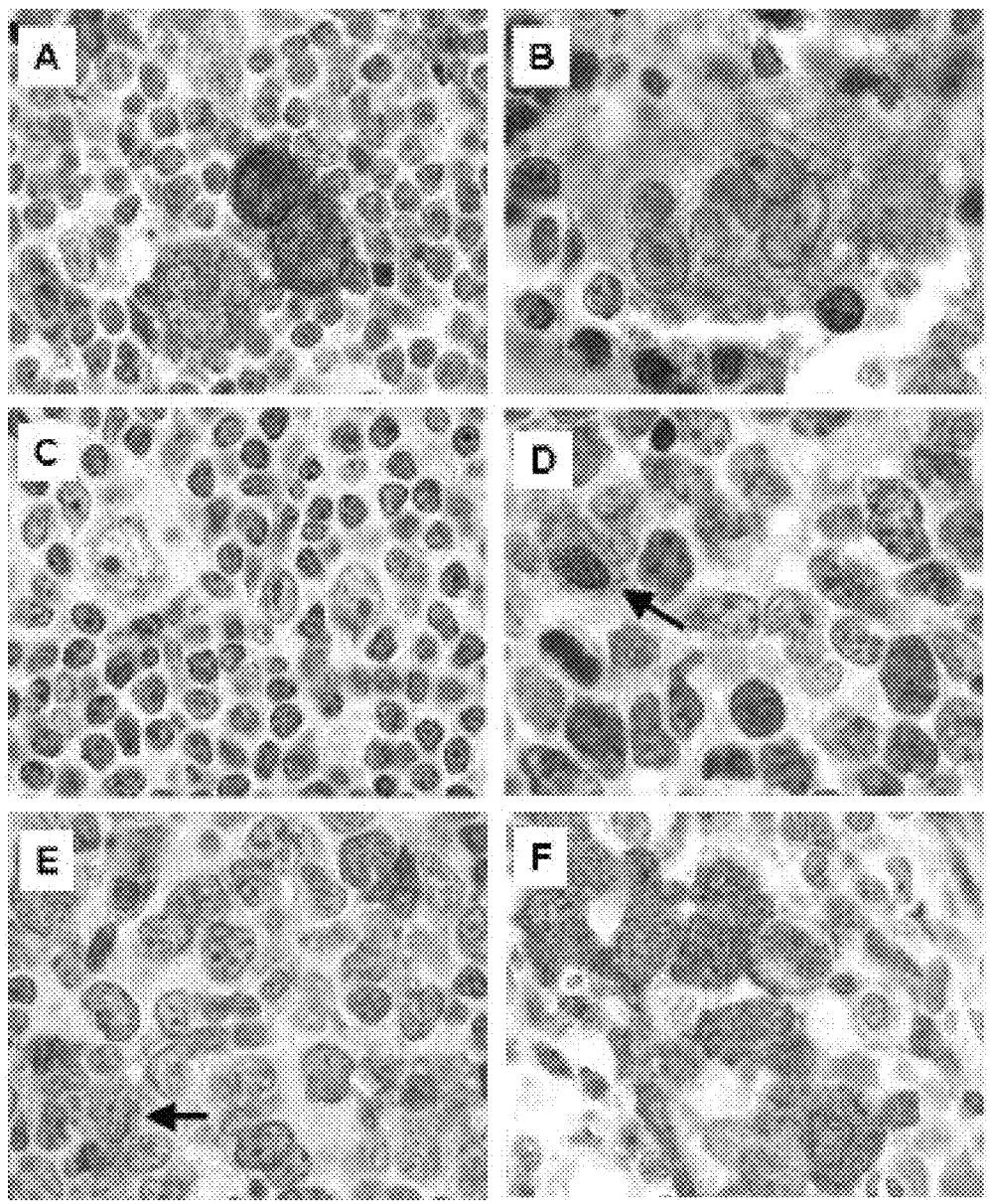
FIG. 4 shows primary human tumor samples stained for Gal1 and photographed at 1000× magnification.

Immunostaining with an antibody known to be specific for Gal1 immunohistochemistry revealed robust staining of the cytoplasmic and weak cell membrane staining of Reed-Sternberg cells in cHL (FIG. 4A). In contrast, the frequent small lymphocytes and occasional granulocytes comprising the inflammatory infiltrate surrounding the Reed-Sternberg cells were negative for Gal1 (FIG. 4A). Scattered intermixed macrophages, dendritic cells, and at least a subset of endothelial cells also showed expression of Gal1. The majority of cases of primary cHLs (61%) exhibited very strong expression of Gal1 (3+ on a scale of 0 to 3 [no staining to very strong staining, respectively], FIG. 4A);

additional cases (31%) exhibited moderate staining scored as 2+ (FIG. 4B). In only rare cases were cHLs negative for Gal1 expression (Table 1). Overall, 66 of 72 cases of cHL (92%) exhibited moderate to strong expression of Gal1 by the RS cells (Table 1, FIGS. 4A and 4B). All of the examined subtypes of cHL were largely Gal1+; similarly, both EBV+ and EBV-tumors expressed this glycan-binding protein (Table 1).

TABLE 1

| Diagnosis | Galectin+ |
| --- | --- |
| cHL- Total* | 66/72 (92%) |
| NSHL | 41/45 (91%) |
| MCHL | 14/15 (93%) |
| LRHL | 1/1 (100%) |
| cHL, nos | 10/11 (91%) |
| NLPHL** | 0/15 (0%) |
| PMLBCL | 2/17 (12%) |
| DLBCL | 7/102 (7%) |
| ALCL^ | 18/19 (95%) | cHL = classical Hodgkin lymphoma, NSHL = nodular sclerosis Hodgkin lymphoma, MCHL = mixed cellularity Hodgkin lymphoma, LRHL = lymphocyte-rich Hodgkin lymphoma, cHL, nos = classical Hodgkin lymphoma, not otherwise specified, NLPHL = nodular lymphocyte-predominant Hodgkin lymphoma, PMLBCL = primary mediastinal large B cell lymphoma, DLBCL = diffuse large B cell lymphoma, ALCL = anaplastic large cell lymphoma.
*8/10 EBV+ cases are Galectin+; 30/33 EBV- cases are Galectin+
**faint golgi staining observed in some cases
^2/11 tested cases ALK-1 positive; 9/11 tested cases ALK-1 negative In contrast to cHLs, none of the nodular lymphocyte-predominant Hodgkin lymphomas (NLPHL) exhibited moderate to strong (2 or 3+) Gal1 expression (FIG. 4C and Table 1). However, certain NLPHLs (9/15 cases, 60%) had weak, focal, perinuclear Gal1 staining suggestive of localization to the Golgi apparatus. This Gal1 immunohistochemical pattern was only detected in a subset of NLPHLs and not observed in any other lymphoid tumors. This difference in Gal1 expression in cHL and NLPHLs are of considerable interest because NLPHLs share certain morphologic features with cHLs but differ in their prognosis.

With emerging data indicating that seemingly disparate tumors such as cHL and primary mediastinal large B-cell lymphoma (PMLBCL) share important molecular features and survival pathways (Savage et al. (2003) Blood 102, 3871-3879), the expression pattern of Gal1 was evaluated in PMLBCL (n=17) and compared these findings to non-mediastinal forms of DLBCL (n=102).

Expression of Gal1 was found in only 2 of 17 cases (12%) of PMLBCL (FIG. 4D; Table 1). Similarly, only 7 of 102 cases of DLBCL (7%) exhibited Gal1 expression (FIG. 4E, Table 1). No distinguishing clinical, morphologic, or phenotypic features among the rare Gal1 positive PMLBCLs or DLBCLs were found upon review. Positive Gal1 immunostaining is, thus, a sensitive and specific marker for distinguishing cHL from PMLBCL (sensitivity=92%; specificity=88%) and delineating cHL from DLBCL (sensitivity=92%; specificity=96%).

ALCLs are aggressive large cell lymphomas of T-cell origin with high levels of c-Jun and JunB expression and constitutive activation of AP1 (Mathas et al. (2002) EMBO J. 21: 4104-4113; Drakos et al. (2007) Am. J. Surg. Pathol. 29:196-203). Given the role of the AP1 pathway in ALCL and the AP1-dependent Gal1 expression in cHL, it was next asked whether ALCLs overexpressed Gal1. Ninety-five percent of primary ALCLs (18 of 19 cases) exhibited moderate to strong (2+ or 3+) diffuse cytoplasmic Gal1 staining (FIG. 4F); both ALK+ and ALK- tumors expressed this glycan-binding protein (Table 1).

The polyclonal antisera recognizing Gal1 that was used in these studies has been well characterized and known to be specific (Rubinstein et al. (2004) Cancer Cell 5:241-251; Juszczynski et al. (2007) Proc. Natl. Acad. Sci. USA 104: 13134-13139). However to validate the observed results, a subset of cases were immunostained with a recently generated, novel affinity-purified antisera specific for Gal1. There was a perfect correlation of staining patterns among Gal1-positive and -negative tumors with these two Gal1 antisera. A subset of cases were also stained with a commercially available antibody that recognizes Gal1 (Gandhi et al (2007) Blood 100: 1326-1329). It was found that the commercial antibody was not as robust as the recently generated antibodies at detecting moderate levels (2+ staining) of Gal1 expression in primary tumor cells.

Example 6: Association Between Gal1 and c-Jun Expression

Given the AP1 dependence of Gal1 in cHL (Juszczynski et al. (2007) Proc. Natl. Acad. Sci. USA 104:13134-13139) and the selective expression of Gal1 in another AP1-driven tumor, ALCL, the co-expression of the AP1 component, c-Jun, and Gal1 in the series of primary lymphomas was assessed.

In agreement with prior reports (Mathas et al. (2002) EMBO J. 21: 4104-4113), it was found that RS cells of all examined primary cHLs expressed nuclear c-Jun (Table 1 and FIG. 5B). In this extensive series of primary cHLs, all examined Gal1+ tumors expressed high levels of c-Jun (Table 2 and representative example, FIGS. 5A and 5B). Almost all examined primary ALCLs also expressed c-Jun, which localized to the nucleus (Table 2 and FIG. 5E). The concordance of Gal1 and c-Jun expression in ALCL (FIGS. 5D and 5E) strongly suggests that c-Jun-mediated signaling could be responsible for near ubiquitous Gal1 expression in this tumor type—a possibility supported by the lack of c-Jun expression in the single ALCL negative for Gal1 (Table 2).

TABLE 2

| Diagnosis | Gal+ and Jun+ | Gal+ and Jun− | Gal− and Jun+ | Gal− and Jun− |
| --- | --- | --- | --- | --- |
| cHL* | 54/60 (90%) | 0/60 (0%) | 6/60 (10%) | 0/60 (0%) |
| NLPHL | 0/15 (0%) | 0/15 (0%) | 2/15 (13%) | 13/15 (87%) |
| PMLBCL | 2/17 (12%) | 0/17 (0%) | 4/17 (24%) | 11/17 (65%) |
| DLBCL | 4/102 (4%) | 3/102 (3%) | 14/102 (14%) | 81/102 (79%) |
| ALCL | 18/19 (95%) | 0/19 (0%) | 0/19 (0%) | 1/19 (5%) | cHL = classical Hodgkin lymphoma, NSHL = nodular sclerosis Hodgkin lymphoma, MCHL = mixed cellularity Hodgkin lymphoma, LRHL = lymphocyte-rich Hodgkin lymphoma, cHL, nos = classical Hodgkin lymphoma, not otherwise specified, NLPHL = nodular lymphocyte-predominant Hodgkin lymphoma, PMLBCL = primary mediastinal large B cell lymphoma, DLBCL = diffuse large B cell lymphoma, ALCL = anaplastic large cell lymphoma.
*cases of cHL for which both galectin-1 and c-Jun staining could be evaluated Among other Hodgkin variants and large cell lymphomas, it was found that c-Jun expression was uncommon. Eighty-seven percent (13/15 cases) of NLPHL, 82% (84/102 cases) of DLBCL, and 65% (11/17 cases) of PMLBCL were negative for c-Jun despite staining of appropriate internal controls (representative DLBCL, FIG. 5H and Table 2). Of note, in the rare Gal1+DLBCLs and PMLBCLs, coexpression of c-Jun was observed (Table 2). More specifically, of the 213 cases immunostained for both Gal1 and c-Jun, only 3 cases (1.4%) showed Gal1 expression in the absence of c-Jun. Taken together, these data reveal a strong association between the presence of Gal1 and the co-expression of nuclear c-Jun, regardless of the lymphoma type.

Figure 5:
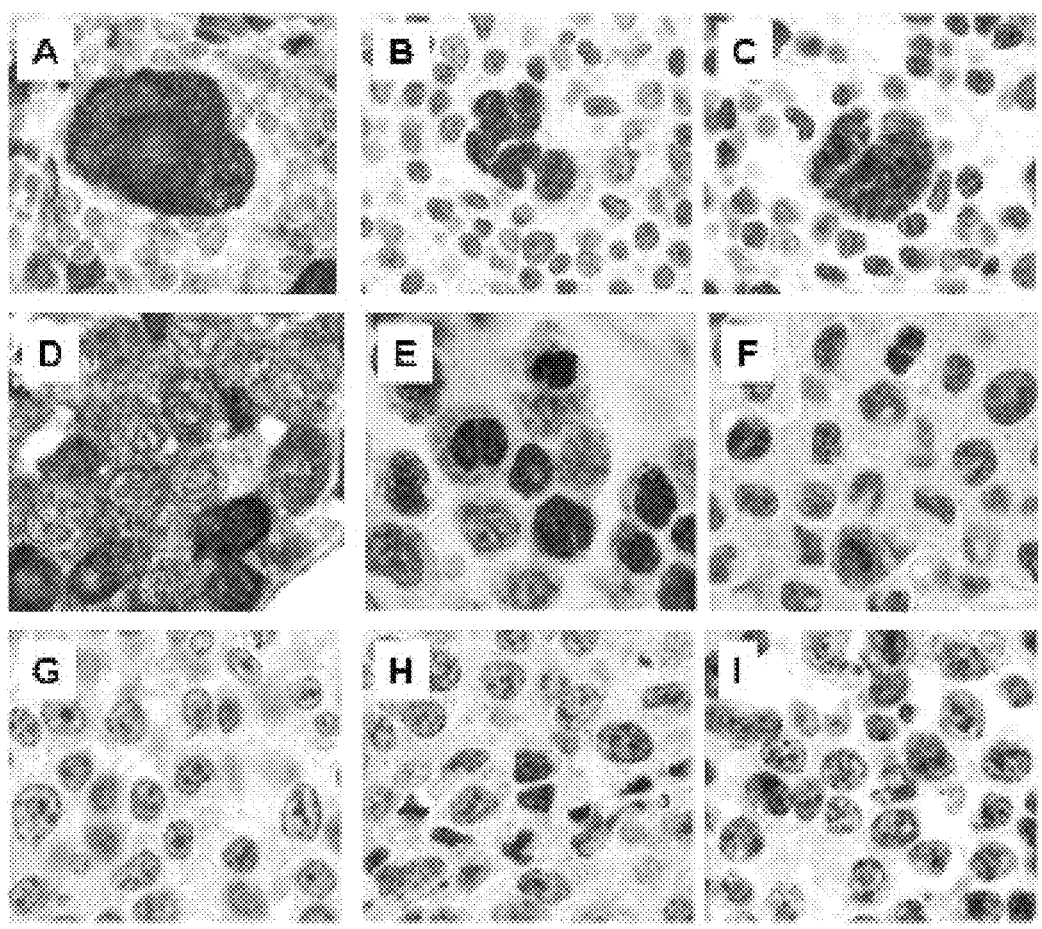
FIG. 5 shows matched primary human tumor samples stained for Gal1 (FIGS. 5A, 5D, 5G), c-jun (FIGS. 5B, 5E, 5H), or c-jun phosphorylated on serine 63 (FIGS. 5C, 5F, 5I) and photographed at 1000× magnification. Reed-Sternberg cells of cHL with positive staining for Gal1 (FIG. 5A), c-Jun (FIG. 5B), and phosphorylated c-Jun (FIG. 5C). Malignant cells of ALCL with positive staining for Gal1 (FIG. 5D), c-Jun (FIG. 5B), and phosphorylated c-Jun (FIG. 5C). Malignant cells of DLBCL with negative staining for Gal1 (FIG. 5G), c-Jun (FIG. 5H), and phosphyorylated c-Jun (FIG. 5I).

Example 7: Association Between Gal1 Expression and Phosphorylated (Activated) c-Jun The transcription factor c-Jun is constitutively expressed in Hodgkin cell lines and primary cHL tumors (Juszczynski et al. (2007) *Proc. Natl. Acad. Sci. USA* 104:13134-13139; Drakos et al. (2007) *Am. J. Surg. Pathol.* 29:196-203), and is a critical component of the AP1 transcriptional complex required for Gal1 expression (Juszczynski et al. (2007) *Proc. Natl. Acad. Sci. USA* 104:13134-13139). To confirm that the c-Jun protein detected by immunohistochemistry is functionally active, a subset of tumors were immunostained with a monoclonal antibody that specifically recognizes the activated form of c-Jun (phospho Ser63 c-Jun) (Derijard et al. (1994) *Cell* 76:1025-1037). In all cases of Gal1+cHL, there was corresponding expression of the activated phosphorylated form of c-Jun in RS cells (FIG. 5C). Similarly, all examined ALCLs expressed both Gal1 and phospho c-Jun (FIG. 5F). The unusual cases of DLBCL and MLBCL that expressed Gal1 also exhibited nuclear c-Jun and phospho c-Jun staining.

Figure 6:
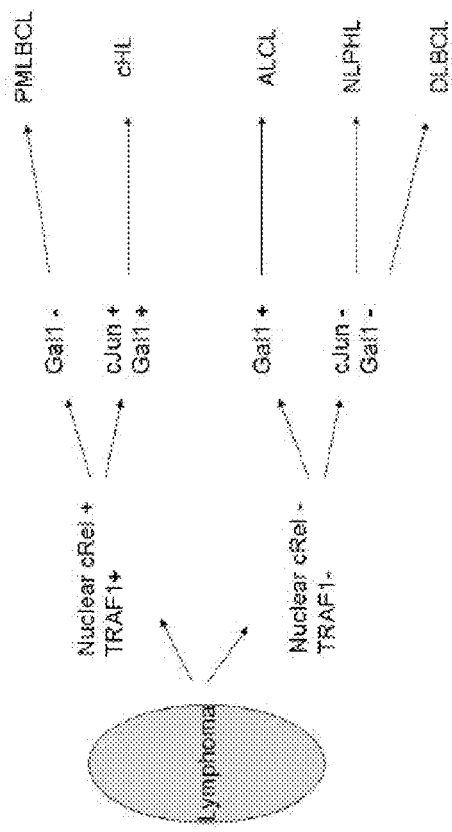
FIG. 6 shows a schematic diagram summarizing an algorithm for the immunohistochemical subclassification of primary mediastinal large B-cell lymphoma (PMLBCL), CHL, NOS(CHL), anaplastic large cell lymphomas (ALCL), diffuse large B-cell lymphoma (DLBCL), and nodular, lymphocyte-predominant Hodgkin lymphoma (NLPHL) using Gal1, c-Jun, Traf1 and nuclear c-Rel. Traf1 and c-Rel immunoreactivity aid in the distinction of cHL and PMLBCL from other lymphomas and Gal1 and c-Jun immunoreactivity help separate cHL and ALCL from PMLBCL, DLBCL and NLPHL.

Thus, immunostaining for the combination of the above-mentioned markers can be used to aid in distinguishing among various cancers (FIG. 6).

Example 8: Expression of Gal1 by MLL-Associated Leukemias

Figure 7:
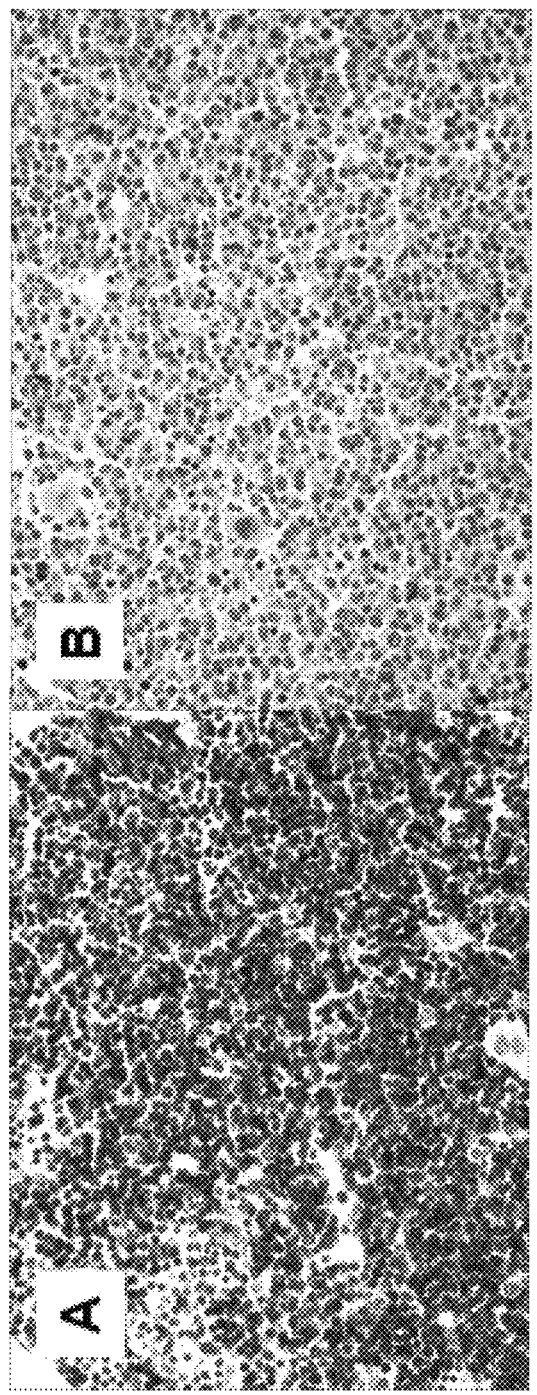
FIG. 7 shows strong expression of Gal1 in MLL-rearranged precursor B-cell ALL (FIG. 7A; MLL$^+$ pre B-cell ALL) and lack of expression of Gal1 in MLL-negative precursor B-cell ALL (FIG. 7B; MLL$^-$ pre B-cell ALL) by immunohistochemistry.

Immunostaining on Zenker's fixed paraffin embedded bone marrow sections revealed strong reactivity in all tumor cells for Gal1 in 10 of 10 (100%) of MLL-rearranged precursor B-cell ALL, but only 1 of 38 (3%) MLL-negative precursor B-cell ALL (Table 3 and FIG. 7). In summary, 100% of acute leukemias with MLL rearrangements showed strong expression of Gal1. In addition, among precursor B-cell Acute ALL, the expression of Gal1 is highly specific for the presence of an MLL rearrangement.

TABLE 3

| Diagnosis | Gal positive |
| --- | --- |
| Pre B ALL MLL+ | 10 of 10 |
| Pre B ALL MLL− | 1 of 38 |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject having anaplastic large cell lymphoma that would benefit from upregulation of an immune response, the method comprising:
   i) having an analysis performed to determine that the subject having anaplastic large cell lymphoma would benefit from upregulation of an immune response comprising
      a) determining the level of expression of galectin-1 (Gal1) in a subject sample;
      b) determining the normal level of expression of Gal1 in a control sample; and
      c) comparing the level of expression of Gal1 in the subject sample to the level of expression of Gal1 in the control sample,
         wherein (1) the subject sample comprises cells from anaplastic large cell lymphoma in the subject, (2) the control sample comprises cells of the same type from a control subject not having anaplastic large cell lymphoma, and (3) the level of expression of Gal1 is assessed by detecting the presence of the Gal1 protein within the cytoplasm of the cells in the samples using an antibody or antigen binding fragment thereof that specifically binds to the Gal1 protein; and
   ii) administering an anti-Gal1 blocking antibody to the subject having anaplastic large cell lymphoma determined to have a significant increase in the level of expression of Gal1 in the subject sample relative to the normal level.

2. The method of claim 1, wherein the anaplastic large cell lymphoma is ALK1 positive.

3. The method of claim 1, wherein the anaplastic large cell lymphoma is ALK1 negative.

4. The method of claim 1, wherein the cells are in bone marrow or a fluid selected from the group consisting of whole blood fluid, interstitial fluid, and lymph fluid.

5. The method of claim 1, wherein the antibody is a monoclonal antibody.

6. The method of claim 1, wherein the antibody is a polyclonal antibody.

7. The method of claim 1, wherein the antibody is a chimeric or a humanized antibody.

8. The method of claim 1, wherein the antibody or antigen binding fragment is a single-chain antibody.

9. The method of claim 1, wherein the antibody or antigen binding fragment is a Fab fragment.

10. The method of claim 1, wherein the antibody or antigen binding fragment thereof is detectably labeled.

11. The method of claim 1, wherein the antibody or antigen binding fragment thereof specifically binds a Gal1 epitope comprising the carbohydrate binding domain.

12. The method of claim 1, wherein the antibody or antigen binding fragment specifically binds a Gal1 epitope comprising amino acids 62-86 of human Gal1.

13. The method of claim 1, wherein the antibody comprises an effector domain.

14. The method of claim 1, wherein the antibody comprises an Fc domain.

15. The method of claim 1, wherein said significant increase is an at least two-fold increase in the level of expression of Gal1 in the subject sample relative to the normal level of expression of Gal1 in the control sample.

16. The method of claim 15, wherein said significant increase is an at least five-fold increase in the level of expression of Gal1 in the subject sample relative to the normal level of expression of Gal1 in the control sample.

* * * * *